(12) United States Patent
Armbruster et al.

(10) Patent No.: US 8,133,694 B2
(45) Date of Patent: Mar. 13, 2012

(54) FUNCTIONAL VITAMIN D DERIVATIVES AND METHOD OF DETERMINING 25-HYDROXY- AND 1α, 25-DIHYDROXY VITAMIN D

(75) Inventors: Franz Paul Armbruster, Bobenheim-Roxheim (DE); Wolfgang Voelter, Tübingen (DE); Jens Tampe, München (DE); Christian Birkmayer, München (DE)

(73) Assignees: Immundiagnostik AG, Bensheim (DE); Biomedica GmbH, Vienna (AT)

( * ) Notice: Subject to any disclaimer, the term of this patent is extended or adjusted under 35 U.S.C. 154(b) by 737 days.

(21) Appl. No.: 10/790,746

(22) Filed: Mar. 3, 2004

(65) Prior Publication Data

US 2005/0014211 A1    Jan. 20, 2005

Related U.S. Application Data

(63) Continuation-in-part of application No. 09/720,338, filed as application No. PCT/EP99/04418 on Jun. 25, 1999, now Pat. No. 6,787,660.

(30) Foreign Application Priority Data

Jun. 25, 1998  (DE) .................................. 198 28 379
Sep. 4, 1998   (DE) .................................. 198 40 435

(51) Int. Cl.
  *G01N 33/53*   (2006.01)
  *G01N 33/532*  (2006.01)
  *C07K 16/00*   (2006.01)
  *C07K 1/14*    (2006.01)

(52) U.S. Cl. ........... 435/7.93; 435/7.1; 435/7.5; 436/56; 436/544; 530/389.8; 530/415

(58) Field of Classification Search .................. 435/7.1, 435/7.5, 7.92, 7.93, 7.94, 975; 436/518, 436/526, 530, 531, 56, 815; 530/402; 552/653
See application file for complete search history.

(56) References Cited

U.S. PATENT DOCUMENTS 6,455,714 B1 * 9/2002 Holick et al. ................. 552/653

FOREIGN PATENT DOCUMENTS

| EP | 0 312 360 A2 | 4/1989 |
| EP | 583945 A2 * | 2/1994 |
| WO | WO 97/24127 A1 | 7/1997 |

OTHER PUBLICATIONS

Kobayashi et al., J. Steroid Biochem. Molec. Biol., vol. 62, No. 1, pp. 79-87, XP002119849 (1997).
T. Higashi et al., Analytica Chimica Acta, vol. 365, No. 1-3, pp. 151-158, XP002119850 (1998).
Roy et al., Steroids, vol. 60, No. 8, pp. 530-533 (1995).
Swamy et al., Protein Expression and Purification, vol. 6, No. 2, pp. 185-186 (1995).

* cited by examiner

*Primary Examiner* — Shafiqul Haq
(74) *Attorney, Agent, or Firm* — Birch, Stewart, Kolasch & Birch, LLP

(57) ABSTRACT

The preparation of vitamin D compounds of formula (I) with a label attached to a spacer group in the 3 position is disclosed.

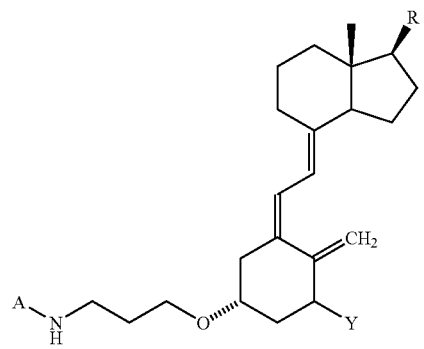

In the above formula (I), O represents the oxygen atom of an ether group; Y represents hydrogen or hydroxy; A represents a label such as biotin, digoxigenin, or another vitamin D group; R represents a substituted hydrocarbon side-group of vitamin D or a vitamin D metabolite. Also disclosed is a method of measuring 25-hydroxy vitamin D metabolite and a 1α,25-dihydroxy vitamin D metabolite in a sample.

11 Claims, 16 Drawing Sheets

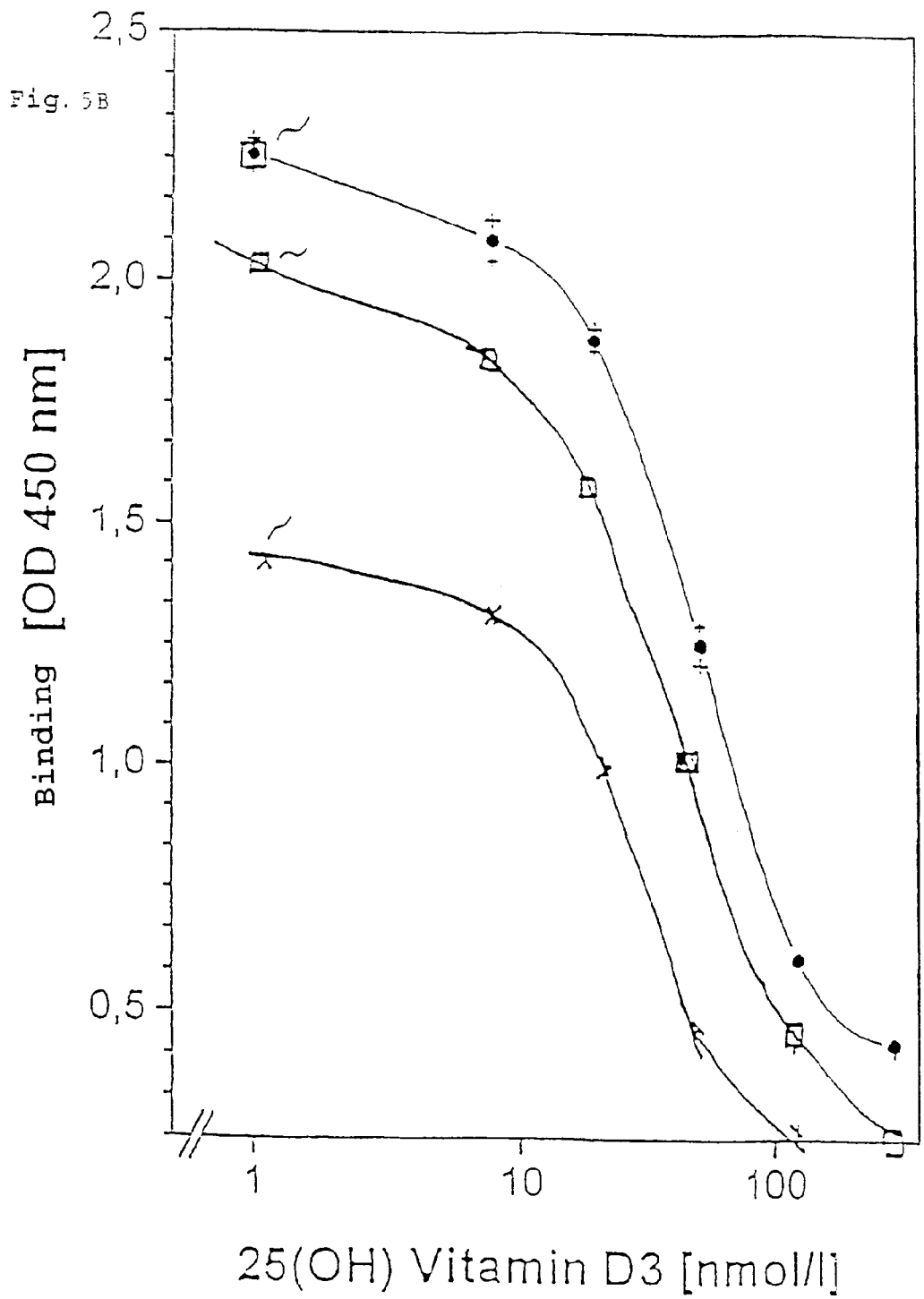

ered States Patent (US 8,133,694 B2)

FUNCTIONAL VITAMIN D DERIVATIVES AND METHOD OF DETERMINING 25-HYDROXY- AND 1α, 25-DIHYDROXY VITAMIN D

CROSS-REFERENCE TO RELATED APPLICATIONS

This application is a Continuation-In-Part of U.S. application Ser. No. 09/720,338, filed Feb. 20, 2001 now U.S. Pat. No. 6,787,600, which is a National Stage Application of PCT International Application No. PCT/EP99/04418 filed on Jun. 25, 1999, which designated the United States, and on which priority is claimed under 35 U.S.C. §120, the entire contents of which are hereby incorporated by reference. This application further claims priority under 35 U.S.C. §119(a)-(d) of application numbers 19828379.2 and 19840435.2 filed in Germany on Jun. 25, 1998 and Sep. 4, 1998, respectively, the entire contents of which are hereby incorporated by reference.

FIELD OF THE INVENTION

The invention relates to a method of obtaining derivatives of 25-hydroxy vitamin D and a method of measuring 25-hydroxy vitamin D and 1,25-dihydroxy vitamin D in samples.

BACKGROUND OF THE INVENTION

The D-vitamins or calciferols arise from their provitamins through a cleavage, catalysed by sunlight, of the B-ring in the sterane rings. Their most important representatives are vitamin $D_3$ (cholecalciferol) and vitamin $D_2$ (ergocalciferol), which differ slightly only in the side chains, but which—so far as known—are similarly metabolised and have identical biological effects. Whereas provitamin $D_2$ must be taken in with the food, the provitamin $D_3$ can be formed in the human organism. So far as not more specifically designated by means of indices, the term vitamin D comprehends in the following in general all vitamin D forms. Vitamin D formed in the skin or taken in with food is bound in the plasma by vitamin D binding or transport proteins (DBP), transported to the liver and there metabolised to 25-hydroxy vitamin D (25-OH-D). The vitamin D binding protein DBP is also known as Gc-globulin or group specific component (J. G. Haddad in J. Steriod Biochem. Molec. Biol. (1995) 53, 579-582). Over 95% of the 25-hydroxy vitamin D measurable in the serum is as a rule 25-hydroxy vitamin D3. 25-Hydroxy vitamin $D_2$ is only found in greater proportions if the person is receiving medication with vitamin $D_2$ or, as is frequently the practice in the United States, foodstuffs are supplemented with vitamin $D_2$.

25-Hydroxy vitamin D is the prevailing vitamin D metabolite in the blood circulation and its concentration in the serum generally indicates the vitamin D status, i.e. the extent to which vitamin D is available to the organism. If needed, 25-hydroxy vitamin D is metabolised in the kidneys to 1α,25-dihydroxy vitamin D, a hormone-like substance with great biological activity. The determination of 1α,25-dihydroxy vitamin D indicates how much vitamin D is present in the activated form.

The determination of 25-hydroxy vitamin D in a sample is preferably effected in accordance with the principle of competitive protein binding analysis, whereby on the basis of the displacement of radioactive 25-hydroxy vitamin D from the binding sites of a vitamin D binding protein, the 25-hydroxy vitamin D present in the sample can be quantified. Also, over the last several years, radioimmunoassays using 125I-labelled vitamin D derivatives and antibodies for vitamin D derivatives have established themselves in diagnosis. The data of the normal level of 25-hydroxy vitamin D in serum vary depending on the laboratory. It is, however, agreed that the concentration of 25-hydroxy vitamin D in the serum is as a rule greater than 5 ng/ml and smaller than 80 ng/ml. The competitive protein binding analysis requires the use of a radioactive vitamin D derivative which must have the same protein binding characteristics as 25-hydroxy vitamin D. The same applies also for the competitive binding analysis for the biologically active 1α,25-dihydroxy vitamin D and other vitamin D metabolites.

European patent specifications 0 312 360 and 0 363 211, and Tanabe et al. in J. Chem. Soc., Chem. Commun. 1989, 1220-1221 and J. Nutri. Sci. Vitaminol., 1991, 37, 139-147, disclose various $^{125}$I-labelled hydroxy- and dihydroxy vitamin D derivatives and their use in binding studies. These derivatives suffer the disadvantages that they are problematic to produce and are extremely labile. Light, radioactive rays, protons, hydrogen, enzymes, free radicals or the presence of iodine in free or bound form have great effect on the configuration and the binding characteristics of the vitamin D derivatives to vitamin D binding protein DBP or specific antibodies. Above all, they can cause or catalyse a rotation of the A-ring in the sterane system. The 3β-hydroxy-group of the vitamin D molecule is thereby rotated into the pseudo-1α-position, so that 5,6-trans-vitamin D is obtained. The so-called pseudo-1α-hydroxy-analogs of vitamin D may be metabolised similarly to vitamin D, but they have a structure which is different in significant points and are not bound or are significantly more poorly bound by vitamin D binding proteins such as for example DBP/Gc-Globulin or anti-vitamin D antibodies.

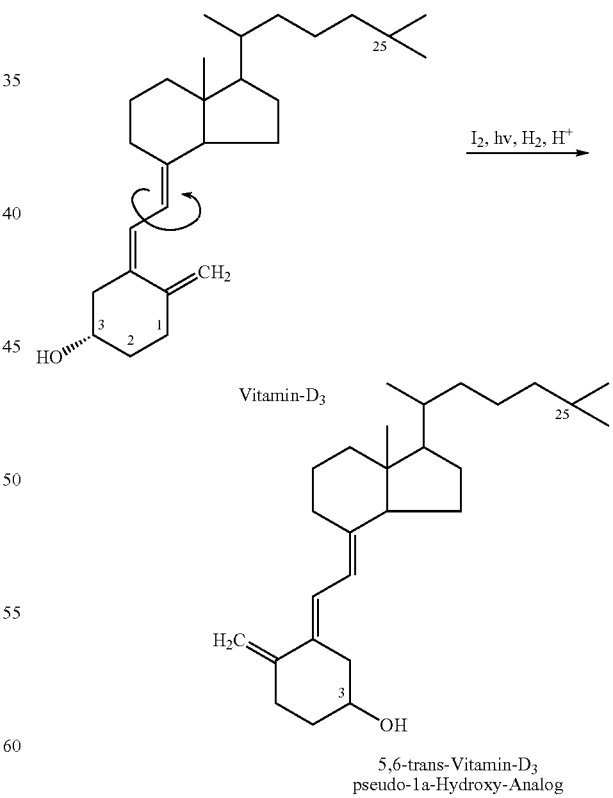

The above-described re-arrangement is to be understood as an example. Other chemical reactions and re-arrangements also occur. The same applies for 3H- or 14C-labelled vitamin D derivatives. These vitamin D derivatives are likewise not so stable that they permit a reliable binding analysis. The radioactive marking additionally increases the costs of storage, transport and disposal and is generally disadvantageous for health and the environment. Further the half-life of $^{125}$iodine is relatively short. On the other hand, a competitive binding analysis with $^3$H- and $^{14}$C-labelled vitamin D derivatives requires particular scintillation counters and is more demanding in terms of equipment, with largely the same problems.

Ray et al., in Biochemistry, 1991, 30, 4809-4813 disclose the coupling of vitamin $D_3$ with various colouring groups. The detection sensitivity for dye-labelled vitamin $D_3$ derivatives is, however, too small that one might use them in a competitive binding analysis for natural vitamin D metabolites, apart from the fact that the dye-labelled derivatives are not stable in serum and further are particularly light-sensitive.

Holick et al, describe in U.S. Pat. No. 5,981,779, issued on Nov. 9, 1999; and WO 97/24127, published on Jul. 10, 1997, with reference to Roy et al in Steroids (1995), 60(8), 530-533 a synthesis scheme said to produce 25-hydroxy-vitamin-$D_3$-aminopropyl-3-(6-amino)-hexanoic acid and its conjugation with biotin-4-nitrophenylester. Example 6 describes that, on a molar basis, about 11 molecules of so synthesised biotin-vitamin-D-conjugate can displace one molecule of $^3$H-25-hydroxy-vitamin-$D_3$ bound to human vitamin D binding protein DBP so that so synthesised molecules can be employed for an enzyme-linked immunosorption assay (ELISA) for measuring the concentration of vitamin $D_3$ and 25-hydroxy-vitamin-$D_3$ in a test solution.

It is the object of the invention to provide vitamin D derivatives, which are more efficient in displacing vitamin D metabolites such as 25-hydroxy vitamin D and 1,25-dihydroxy vitamin D bound to vitamin D binding protein DBP to allow a more precise measurement of those by a competitive immunoassays.

This presumes the following properties: first, that for the vitamin D derivatives, a detection sensitivity exists which is higher than, or lies in a lower range of concentrations than, the concentration of the sought after vitamin D metabolites in the samples; second, that the derivatives are stable in serum, plasma or urine under the usual protonic conditions and are stable with the respect to serum enzymes; third, that the derivatives are sufficiently stable with regard to light and storage, over weeks and months, and finally, that the 25-hydroxy-group of the vitamin D derivative is intact and not tampered by the synthesis.

SUMMARY OF THE INVENTION

This object is achieved by means of vitamin D derivatives having the formula

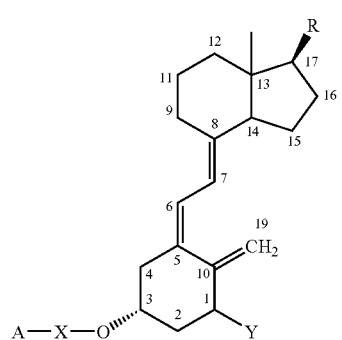

(I)

wherein:

O represents the oxygen atom of an ether group;

x represents a substituted or non-substituted hydrocarbon group of 0.8 to 4.2 nm length, preferably a C8- to C12-group, which may have the usual heteroatoms such as S, O, N or P, most particularly preferred an hexamido-, octamido- or decamido-amidopropylether linker group;

Y represents hydrogen or a hydroxy group;

A a functional group which is bound with high affinity by a binding protein such as an antibody or vitamin D binding protein DBP;

R the side group of a vitamin D metabolite, preferably the side group of vitamin $D_2$ or $D_3$, particularly preferably the 25-hydroxylated side group of vitamin $D_2$ or $D_3$.

A high affinity is present when the dissociation constant (K) between the binding protein, e.g. the antibody or DBP, and the antigen or the functional group A is greater than 108. A dissociation constant greater than 1016 is advantageous for many applications. In a preferred embodiment A is selected from biotin, digoxigenin, tyrosine, substituted tyrosine, substituted amino acids, characteristic amino acid and peptide sequences, FITC, proteins and protein groups such as protein A and protein G or a further vitamin D derivative, most particularly preferred 25-hydroxy vitamin D.

The spacer group X is preferably selected from substituted and non-substituted C-bodies having a length of 0.8 to 4.2 nm, preferably about 0.12 nm. Particularly preferred is an amino carboxylic acid, in particular an amino undecanoic acid, peptide and keto group or a substituted or non-substituted amino polyether radical having a length of 0.8 to 4.2 nm, preferably about 0.9 to 1.5 nm. This spacing between the group A and the binding or detection site for the vitamin D radical is necessary so that the binding proteins can bind to the binding site concerned in each case and thereby do not interfere with one another. It is to be taken into consideration that for example for the vitamin D binding protein DBP (Gc-globulin) the 19-methylene group, if applicable the 1-hydroxy group of the A-ring and the vitamin D side chain belong to the recognition site and are received in a binding pocket. Similar applies also for specific antibodies against the various vitamin D derivatives. If the spacer group X is too short no further binding protein can bind to the selected functional group A along with the vitamin D binding protein. For the preferred example, this means that when the functional biotin group is located within the binding pocket of the vitamin D binding protein it is no longer accessible for the second binding protein, for example the streptavidin. On the other hand, if the spacer group X is too long, molecular folding can arise which likewise hinders the simultaneous binding of two binding partners.

Further, the spacer group in accordance with the invention surprisingly has a steric effect, since it clearly actively hinders a 180E degree rotation of the A-ring. It is suspected, without being restricted to this theory, that the 3β-oxygen atom of the ether group on the A-ring is hydrated corresponding to a natural hydroxy group and so prevents an attack on the 5,6-double bond, apart from other electronic and steric effects. A further important aspect is that the ether group cannot be dissociated by the esterases which are always present in serum or plasma.

Most particularly preferred is 25-hydroxy vitamin-D$_3$-3β-3'[6-N-(biotinyl)hexamido]amidopropylether of the formula II

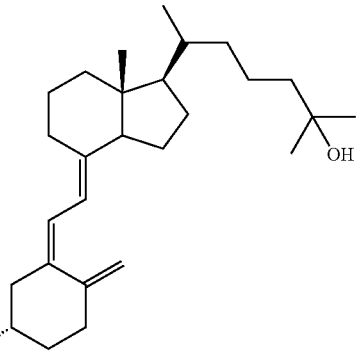

(II)

and the 1α-hydroxy- and vitamin D$_2$ analogs.

Further preferred are derivatives which contain as the second functional group a vitamin D radical. The advantage of these derivatives is that they contain no groups and compounds foreign to the system and so allow an increased sensitivity and reliability of the competitive binding analysis, also because they compensate, in a quantitative detection, for possible binding peculiarities of first and second binding of the vitamin D binding protein. Particularly preferred are compounds of the following formula III:

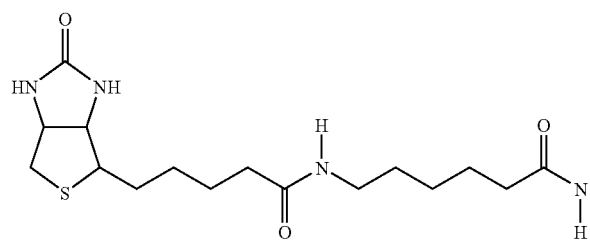

(III)

wherein R, Y and X are defined as in formula I above. Thereby, symmetrical vitamin D derivatives are particularly favourable.

The 25-hydroxy- and 1α,25-dihydroxy vitamin D derivatives in accordance with the invention are surprisingly stable with respect to light, storage and serum and allow in all competitive immune diagnostic methods a sensitive, reliable quantitative determination of vitamin D metabolites such as 25-hydroxy- and 1α,25-dihydroxy vitamin D, for example for routine diagnostic use in human or veterinary medicine and in research.

In accordance with the invention the compound having formula I is obtained by means of a method including the steps: a) cyanoethyling the 3-hydroxy group of vitamin D or 25-hydroxy vitamin D with acrylonitrile in a suitable solvent such as acetonitrile in the presence of potassium hydride and tertiary butanol; b) reducing the resulting nitrile group with a mixture of lithium hydrid and lithium aluminium hydride to an amine; and c) linking a spacer group, if appropriate with a functional group A, to the amine, for example biotinylation of the compound with an active biotinylation reagent such as LC-BHNS or, to obtain a vitamin D derivative in accordance with formula III, coupling of two amino-vitamin D groups by condensing with a dicarboxylic acid such as sebacinic acid, by means of carbodiimide.

The method in accordance with the invention for the production of functional vitamin D derivatives gives higher yields with shorter reaction times. Different from conventional methods, there is effected namely in step a) the cyanoethylation of the 3-hydroxy group in the presence of potassium hydride and tertiary butanol. By this step it is achieved that cyanoethylation is effected only at the 3-hydroxy group of vitamin D and the other hydroxy groups of the vitamin D are protected from reaction. The reaction is effected at 0 to 20EC, preferably at 5 to 8EC in a neutral solvent medium such as acetonitrile.

In the subsequent reduction, the nitrile group of the cyanoethylether is quantitatively reduced into the amine, which can then be relatively simply linked with another functional group, for example by means of reaction with a commercial available biotinylation reagent.

The invention includes additionally the use of the functional vitamin D derivatives in accordance with the invention in methods for detecting 25-hydroxy- and 1α,25-dihydroxy vitamin D in serum, plasma, urine or another sample. Here, the functional vitamin D conjugate in accordance with the invention is employed either as an intermediate, whereby the vitamin D binding protein and native vitamin D metabolites compete for the binding site, or is employed itself as competitive binding component to native vitamin D. The quantitative detection method is preferably an EIA (enzyme immunoassay), ELISA (enzyme-linked immunosorbent assay), RIA (radio immunoassay), IRMA (immuno radiometric assay), LiA (luminescence immunoassay) or ILMA (immuno luminometric assay), FIA (fluorescence immunoassay) or IFMA (immunofluorometric assay) in test systems which are to be worked manually or in versions adapted to automatic testing machines, in liquid phase as well as solid phase technology.

A particularly preferred method for detecting 25-hydroxy- and 1α,25-dihydroxy vitamin D derivatives include the steps: a) coating a carrier with streptavidin, b) addition of one or a plurality of a multifunctional biotin-vitamin D derivatives, c) addition of the sample and a defined quantity of vitamin D binding protein, d) detection of the bound binding protein with labelled anti-vitamin D binding protein antibodies. The labelling of the anti-vitamin D binding protein antibodies can be direct, for example a radioactive marking, or also indirect, for example by an enzyme or an active enzyme fragment such as peroxidase, which is capable of catalysing a colour reaction.

A further preferred method for detecting 25-hydroxy- and 1α,25-dihydroxy vitamin D derivatives includes the steps: a) coating a carrier with anti-vitamin D binding protein antibodies, b) adding the vitamin D binding protein, c) adding the sample and a defined quantity of biotin-vitamin D derivative, d) detecting the quantity of bound derivative with labelled streptavidin. The streptavidin is preferably indirectly labelled with peroxidase; the carrier is preferably a reaction vial wall, for example of a microtitration plate, or particles of polymer or magnetic material or both, for example plastic or cellulose microparticles.

These methods make possible a non-radioactive quantitative detection of 25-hydroxy- and 1,25-dihydroxy vitamin D, without extensive safety measures being required. The competitive methods proposed here are thus suitable for routine investigations within in the scope of osteoporosis prophylaxis, in the case of a suspected D-hypovitaminosis or D-hypervitaminosis, for diagnostics in general, and in research.

A further aspect of the invention is a kit for detecting vitamin D metabolites such as 25-hydroxy- and 1,25-dihydroxy vitamin D, which inter alia contains the functional vitamin D derivative in accordance with the invention. The kit includes a vitamin D binding protein (Gc-globulin) which can be freely selected, anti-vitamin D binding protein antibodies, streptavidin and pre-prepared or non-pre-prepared microtitration plates and/or magnetic or other microparticles and other reagents.

BRIEF DESCRIPTION OF THE DRAWINGS

Further advantages, features and embodiments of the invention are indicated in the following examples and the accompanying drawings, which show:

FIG. 5B calibration curves for ELISAs in accordance with FIG. 5A, having 3, 60 and 100 days old 25-OH-vitamin D biotin tracer;

DETAILED DESCRIPTION OF THE INVENTION

Figure 1:
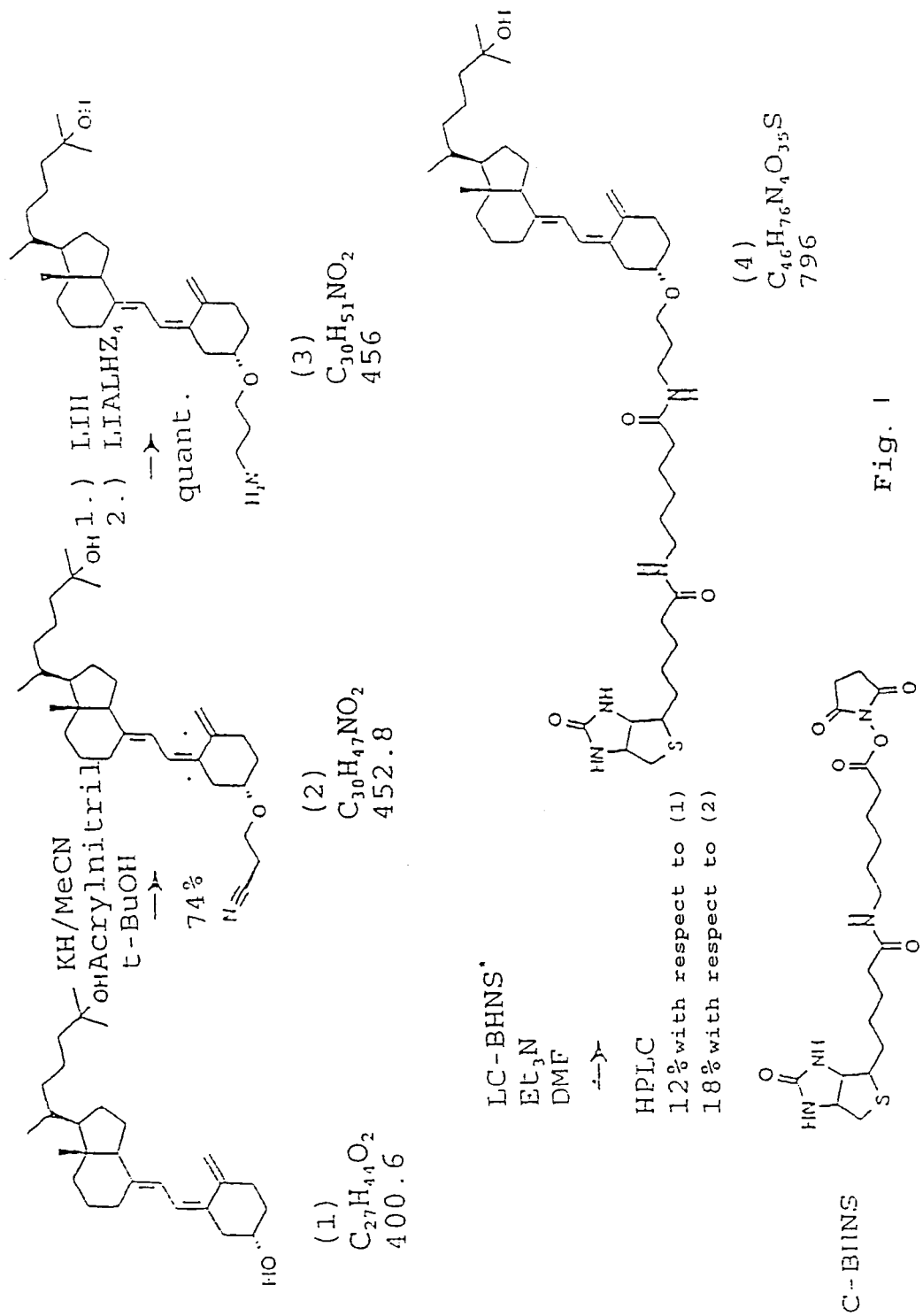
FIG. 1 the schematic path of synthesis for the bifunctional vitamin D derivative 25-hydroxy vitamin-$D_3$-3β-3'[6-N-(biotinyl)hexamido]amidopropylether) in accordance with the invention.

FIG. 1 shows the route of synthesis in accordance with the invention for the production of a bifunctional 25-OH vitamin D conjugate. First, 25-OH vitamin D is cyanoethylated in a mixture of acetonitrile, potassium hydride, and tertiary butanol with acrylonitrile. Due to the presence of the potassium hydride, acting as a base, and due to the presence of tertiary butanol for avoiding non-specific reactions at the 25-hydroxy group, it is achieved that the 3-hydroxy group of the vitamin D is selectively cyanoethylated. The yield of 25-OH vitamin D-3β-cyanoethylether amounts, as a rule, to about 74% with a reaction time of 40 minutes.

After preparation, the 25-OH vitamin D-3β-cyanoethylether is mixed with lithium hydride and the 25-hydroxy group converted into the lithium alcoholate. There follows a reduction of the nitrile with $LiAlH_4$ to 25-OH-vitamin-D-3β-3'-amino propylether. This step is quantitative, without by-products arising. Finally there is effected if necessary a biotinylation with an active biotinylation reagent such as LC-BHNS (biotinyl-N-ε-amino caproyl-hydroxy-succinimide ester). The resulting spacer group X has, corresponding to the amino caproyl chain, a length of about 0.8 to 0.9 nm.

25-OH-vitamin-D-3β-3'[6-N-biotinyl) hexamido] amidopropylether is temperature stable and can be stored over many months in an aqueous, slightly acid matrix. Since the compound cannot be cleaved by serum enzymes, it is ideally suited for routine diagnostic tests in serum, plasma and urine.

Figure 2:
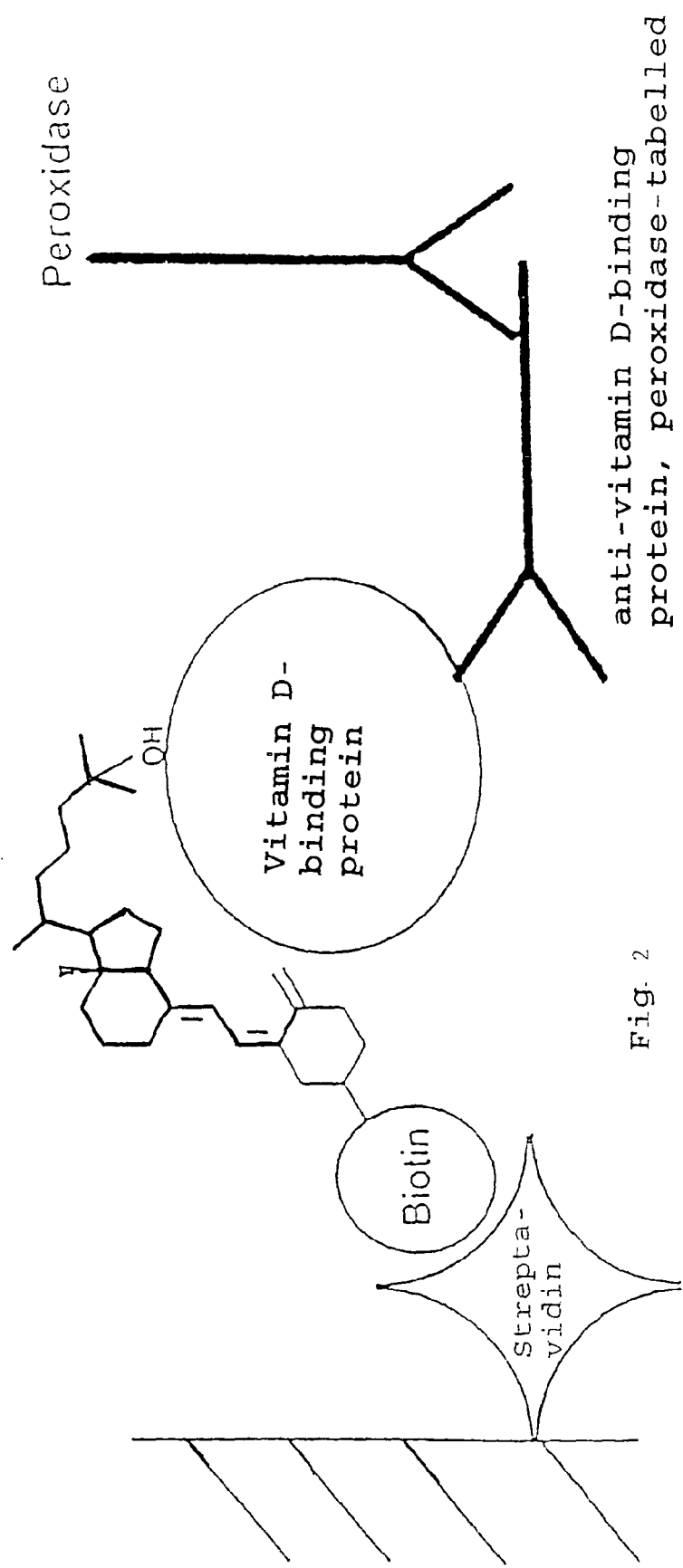
FIG. 2, 3 and 4 schematic representations of various ELISAs for the detection of 25-OH-vitamin D employing 25-OH-vitamin D conjugate in accordance with the invention as binding partner.

FIG. 2 shows a schematic representation of a competitive ELISA for 25-OH-vitamin D. Here, the 25-OH-vitamin D conjugate (25-OH-vitamin-D-3β-3'[6-N-(biotinyl)-hexamido]amidopropylether) is bound via streptavidin to a solid phase. Then, in liquid phase, there is effected the competitive binding of vitamin D binding protein and 25-OH-vitamin D from a standard or a sample to the 25-OH-vitamin D conjugate. The detection is effected by means of peroxidase labelled antibodies against the vitamin D binding protein. The skilled person knows that also other marker enzymes can be employed, for example alkaline phosphatase or galactosidase, etc.

Figure 3:
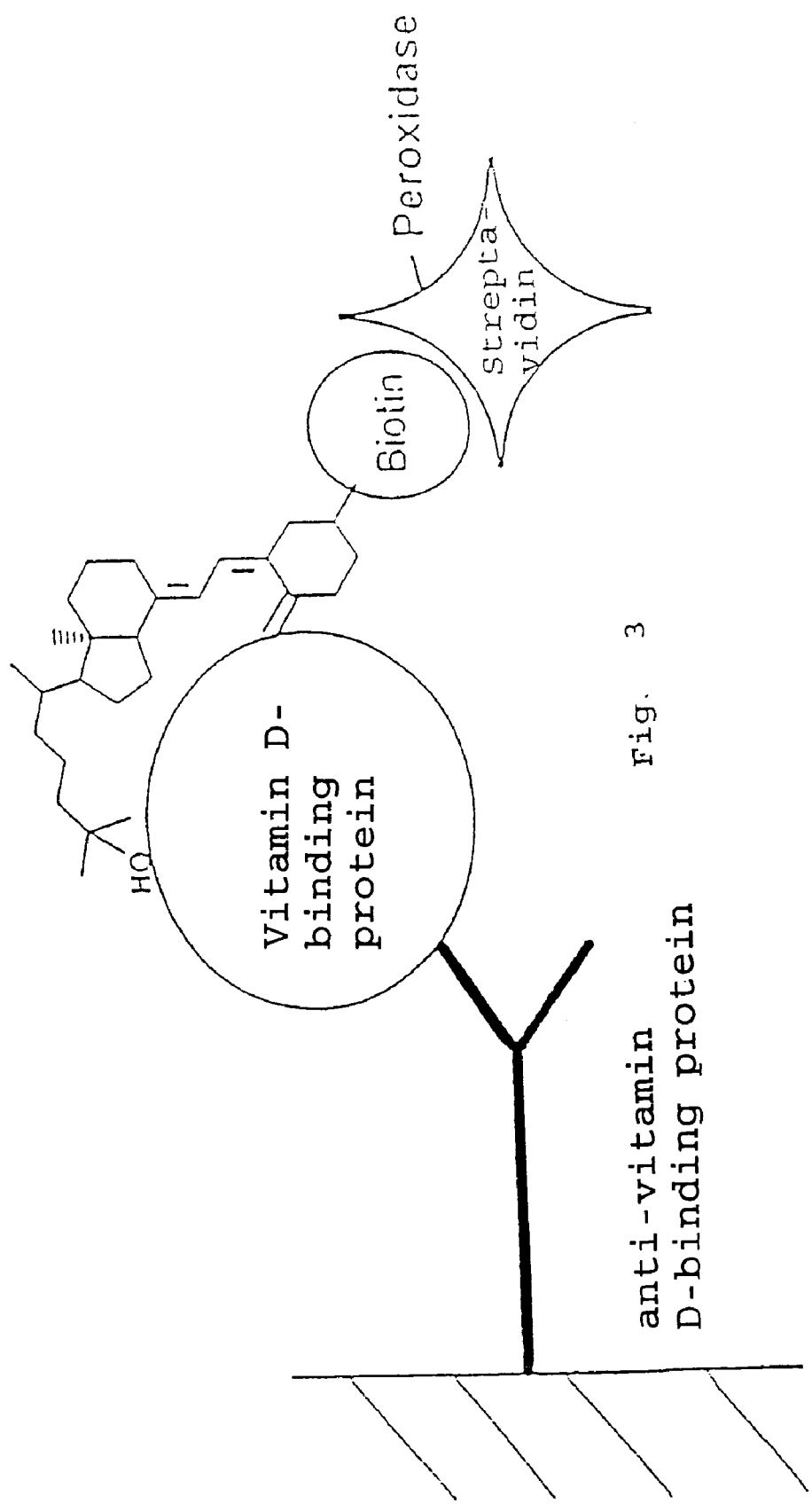

FIG. 3 shows a schematic representation of a competitive, non-radioactive ELISA whereby the vitamin D binding protein is first bound to the solid phase via anti-vitamin D binding protein antibodies. There is then effected, in liquid phase, a competitive binding of 25-OH-vitamin D biotin and 25-OH-vitamin D from a standard or a sample. For detection, peroxidase-labelled streptavidin is then employed. The indicated principle can of course be transferred to other tracer groups instead of biotin and to other marker enzymes, as indicated above.

Figure 4:
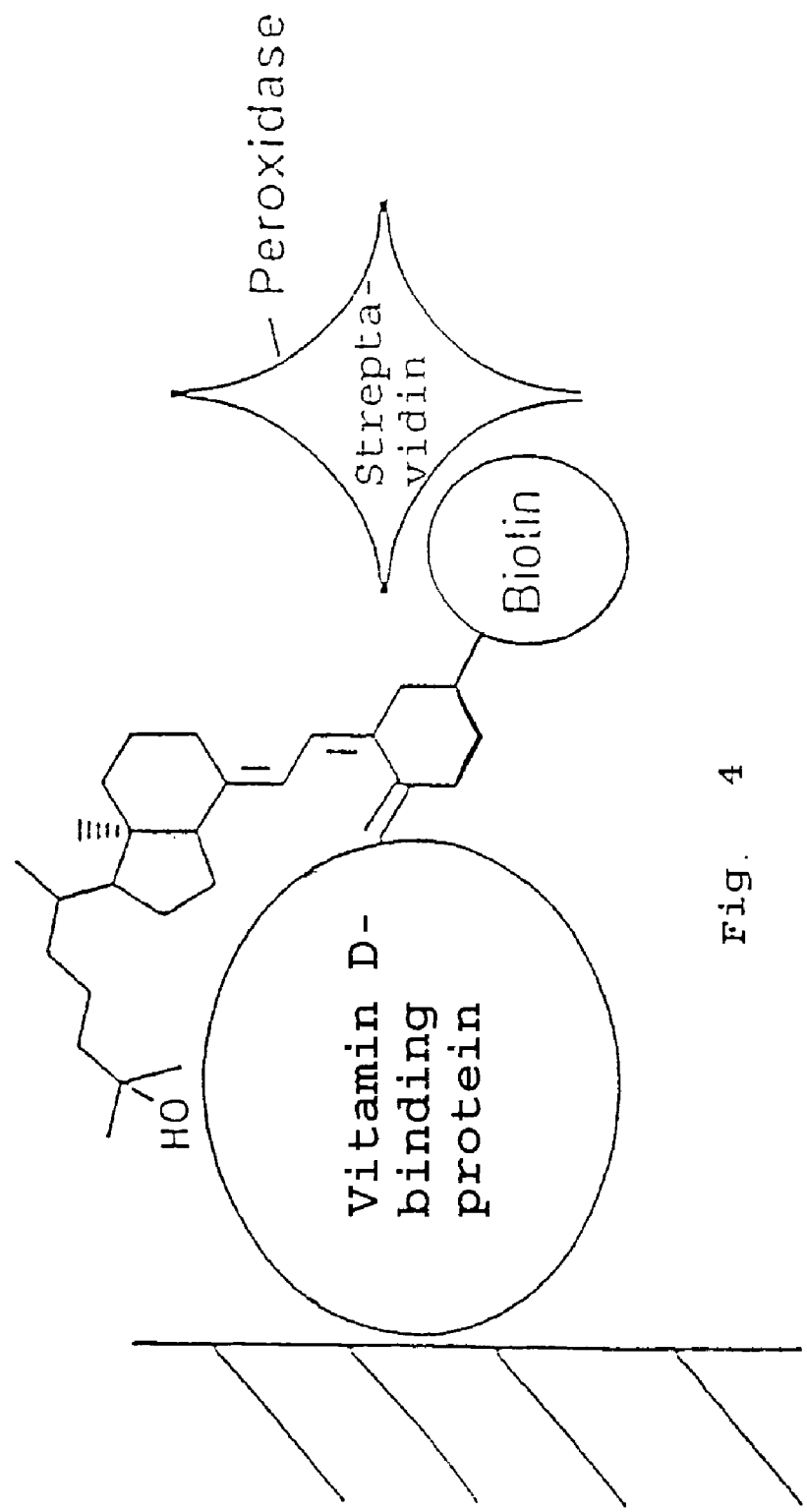

FIG. 4 shows a schematic representation of a competitive ELISA, whereby the vitamin D binding protein is directly bound to the solid phase. The competitive binding of 25-OH-vitamin $D_3$-biotin and 25-OH-vitamin $D_3$ from a standard or a sample is effected in liquid phase and peroxidase-labelled streptavidin is employed for quantitative detection.

Figure 5A:
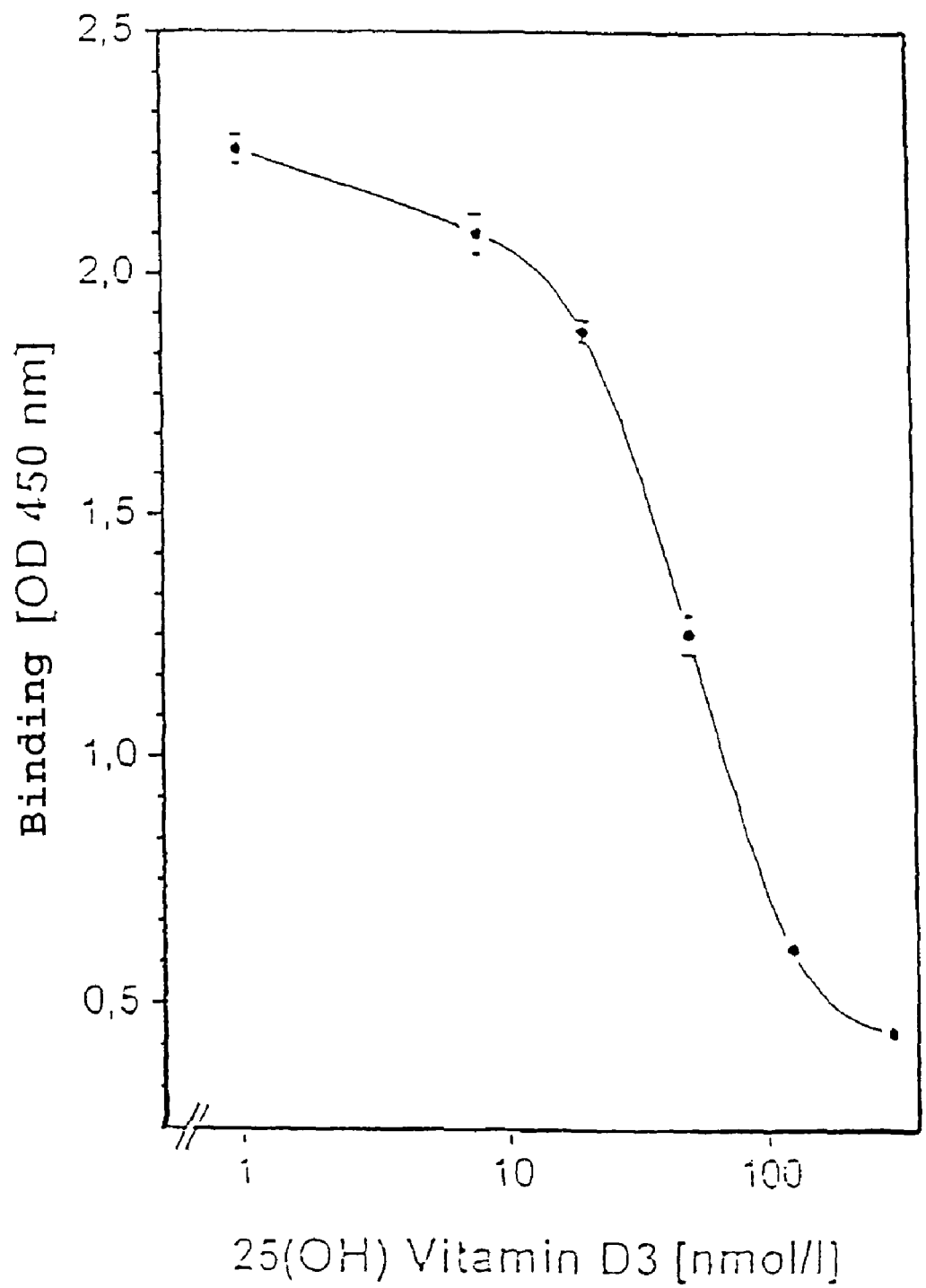
FIG. 5A the calibration curve of a competitive ELISA for 25-OH-vitamin D according to FIG. 2.
Figure 5C:
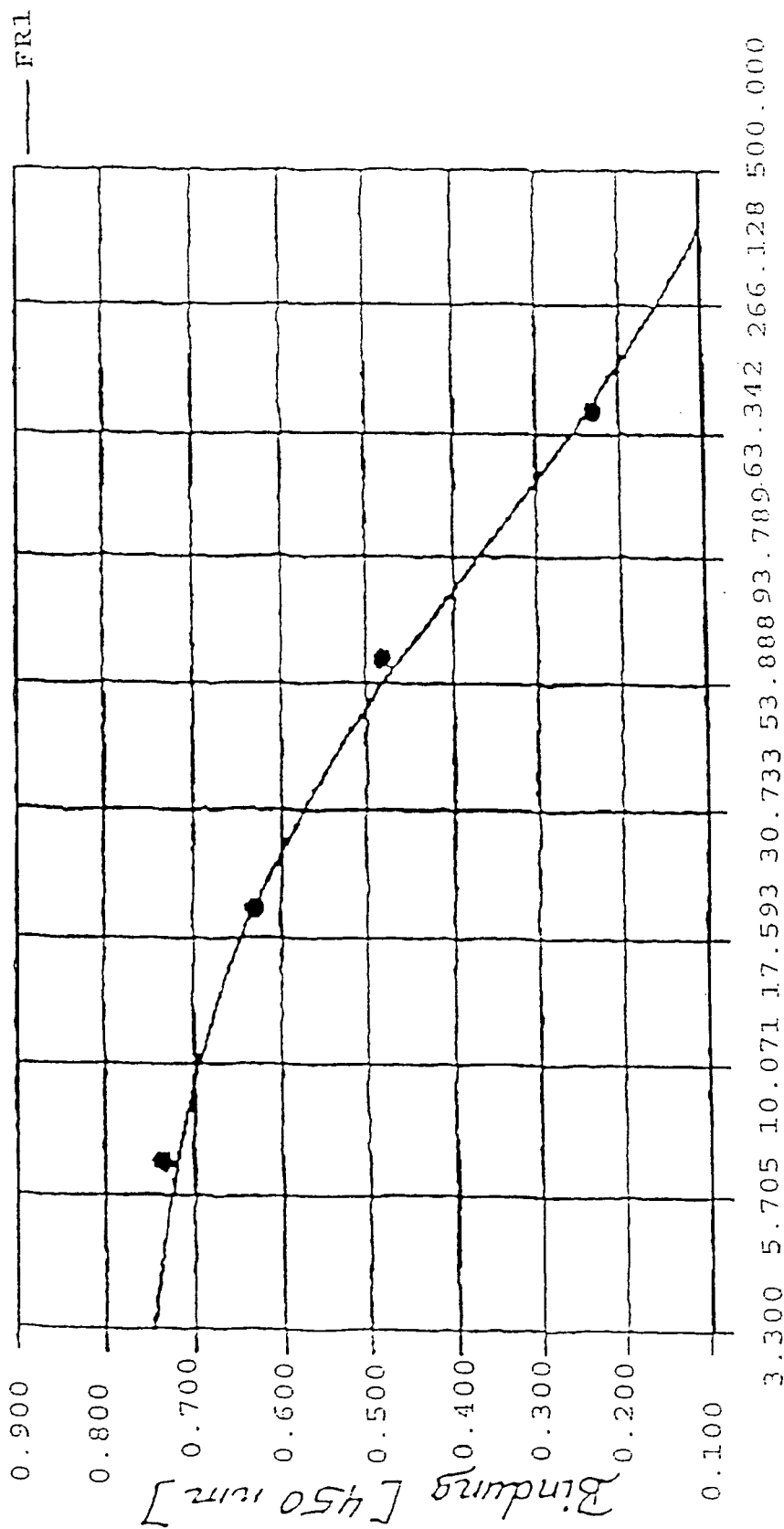
FIG. 5C the calibration curve of a competitive ELISAs for 1,25-dihydroxy vitamin D, analogous to FIG. 2.

FIG. 5A-C show the typical calibration curves of competitive ELISAs with 25-OH— or 1,25-dihydroxy vitamin-$D_3$-biotin, in accordance with the principle shown in FIG. 2. The quantity of bound vitamin D binding protein was determined by means of a standardised colour reaction with peroxidase-coupled anti-vitamin D binding protein antibodies and tetramethylbenzidine (TMB) as substrate. Alternative substrates would be, for example, OPD (1,2-phenyldiamine×2 HCl), ABTS and others. For the calibration curve, vitamin D samples with concentrations of 0, 8, 20, 50, 125 and 312 nMol/l were employed. The ordinate shows the optical density as the mean value of two measurements at 450 nm; the abscissa shows the concentration of 25-OH- or 1,25-dihydroxy vitamin D in nMol/l.

Figure 6:
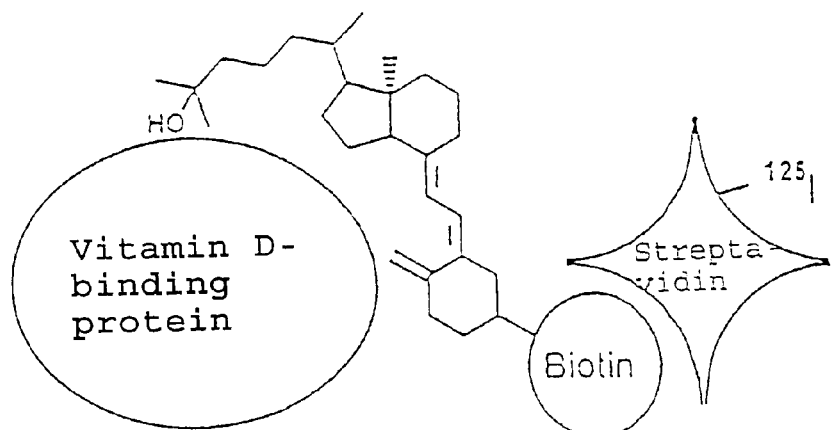
FIGS. 6 and 7 schematic representations of competitive RIAs for 25-OH-vitamin D with the aid of the 25-OH-vitamin D conjugate in accordance with the invention.

FIG. 6 shows the schematic representation of a competitive protein binding test (CPBA), wherein 25-OH-vitamin-$D_3$-biotin and 25-OH-vitamin D, from a standard or sample, compete in liquid phase for the binding site of the vitamin D binding protein. $^{125}$I-labelled streptavidin is employed for the quantitative detection.

Figure 7:
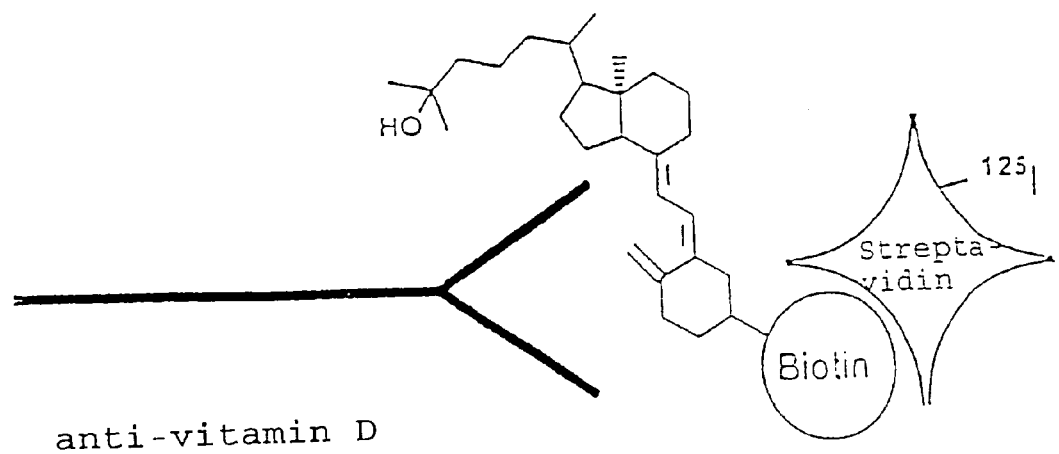

FIG. 7 shows the schematic representation of a competitive radioimmunoassay (RIA), wherein 25-OH-vitamin-D-biotin and 25-OH-vitamin D from a standard or a sample compete in liquid phase for the binding site of an anti-vitamin D-antibody. $^{125}$I-labelled streptavidin is employed for quantitative detection. If the detection is effected by means of a streptavidin which is not radioactive but is labelled with a fluorophore or luminophore, so-called LIA or FIA assays are involved.

Figure 8:
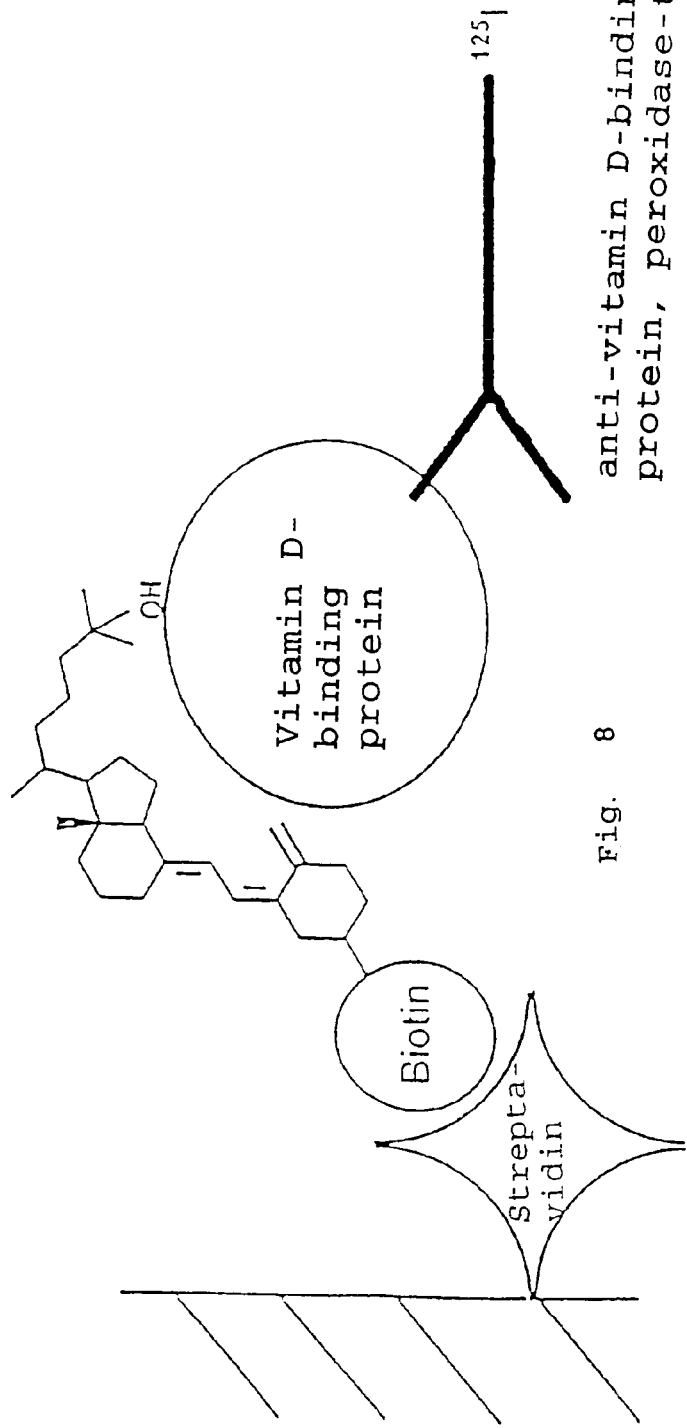
FIG. 8, 9 and 10 schematic representations of competitive, radioactive IRMAs for 25-OH-vitamin D employing the 25-OH-vitamin D conjugate in accordance with the invention as binding partner.

FIG. 8 shows schematic representation of a 25-OH-vitamin D-IRMA. First, 25-OH-vitamin-D-biotin is bound to the solid phase via streptavidin. The competitive binding of vitamin D-binding protein to the conjugate and 25-OH-vitamin-$D_3$ from a standard or a sample is then effected in liquid phase. The quantity of the conjugate-bound binding protein is determined with $^{125}$I-labelled antibodies.

Figure 9:
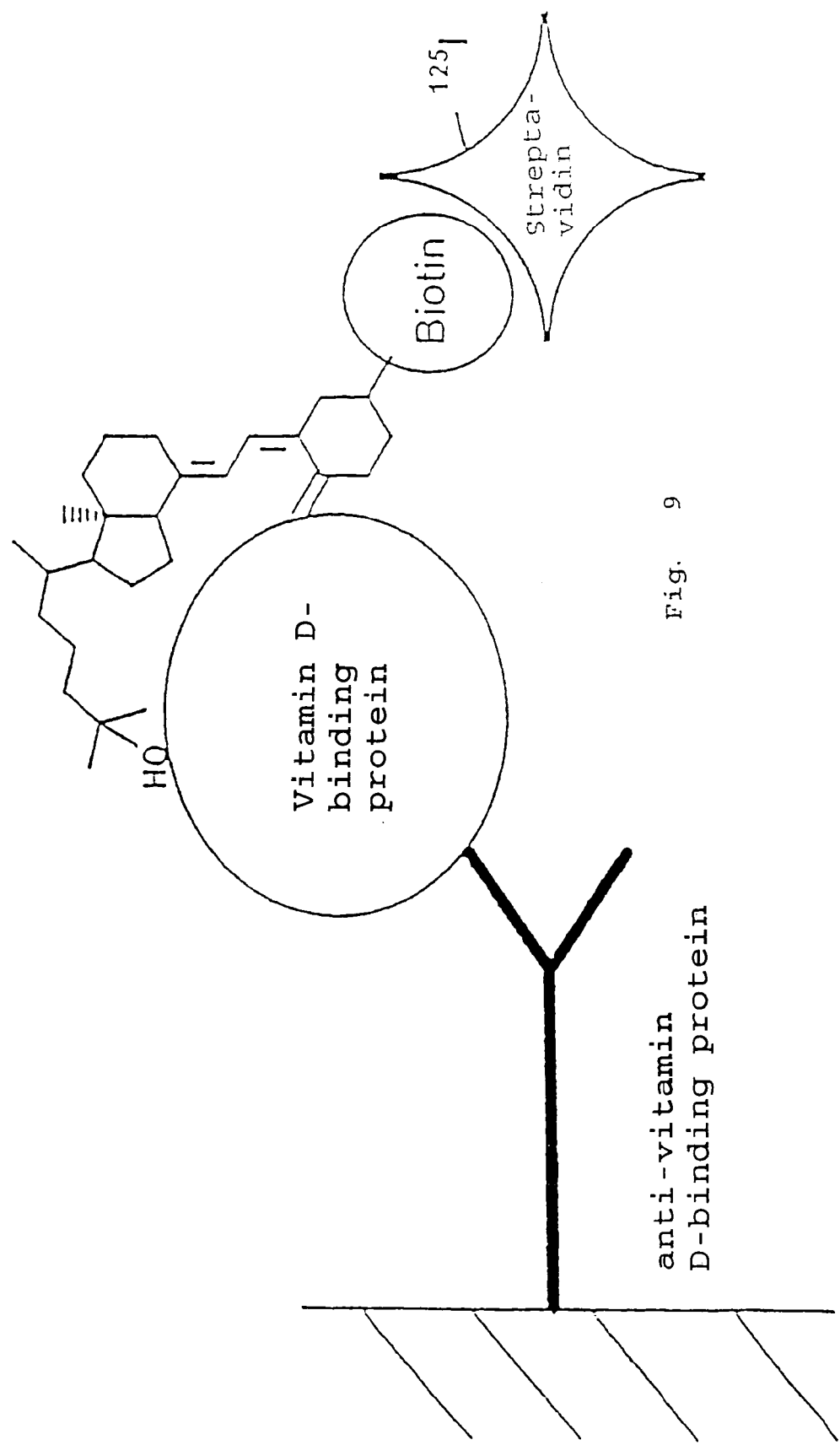

FIG. 9 is the schematic representation of an IRMA sandwich technique (immunoradiometric assay). For this purpose, anti-vit.$D_3$ antibodies are coupled to the solid phase. Vit.D binding proteins then bound to these. The competition takes place in the next step between the 25-OH-vit.D conjugate and 25-OH-vit.D from a standard or a sample. The determination of the quantity of the bound conjugate is effected using $^{125}$I-labelled streptavidin.

Figure 10:
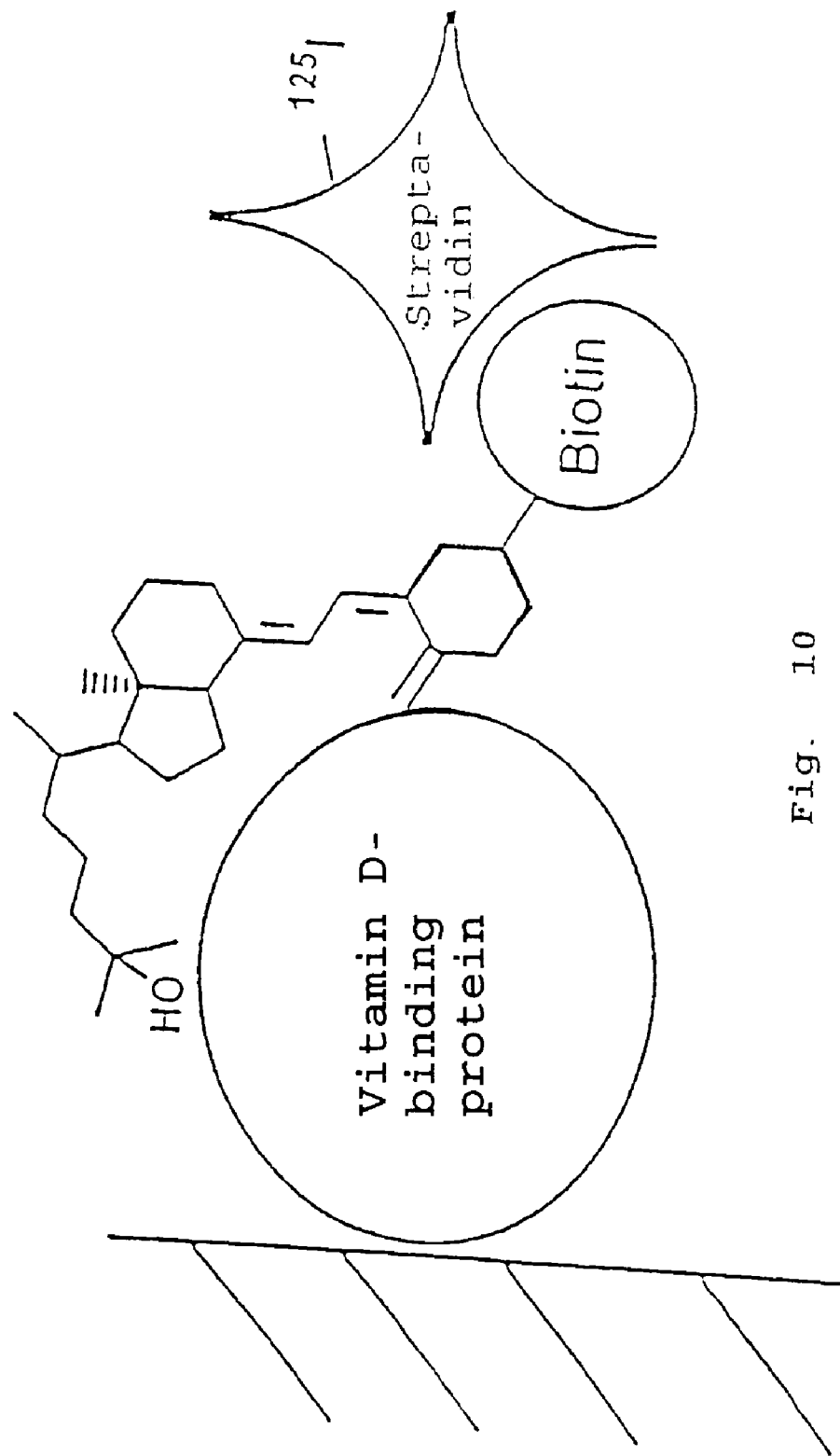

FIG. 10 shows the schematic representation of a further IRMA sandwich technique. First, vitamin $D_3$ binding proteins are coupled to the solid phase. There is then effected thereupon the competitive binding between the 25-OH-vitamin $D_3$ conjugate and 25-OH-vitamin $D_3$ from a standard or a sample. The quantity of bound conjugate is determined by means of $^{125}$I-labelled streptavidin.

Figure 11:
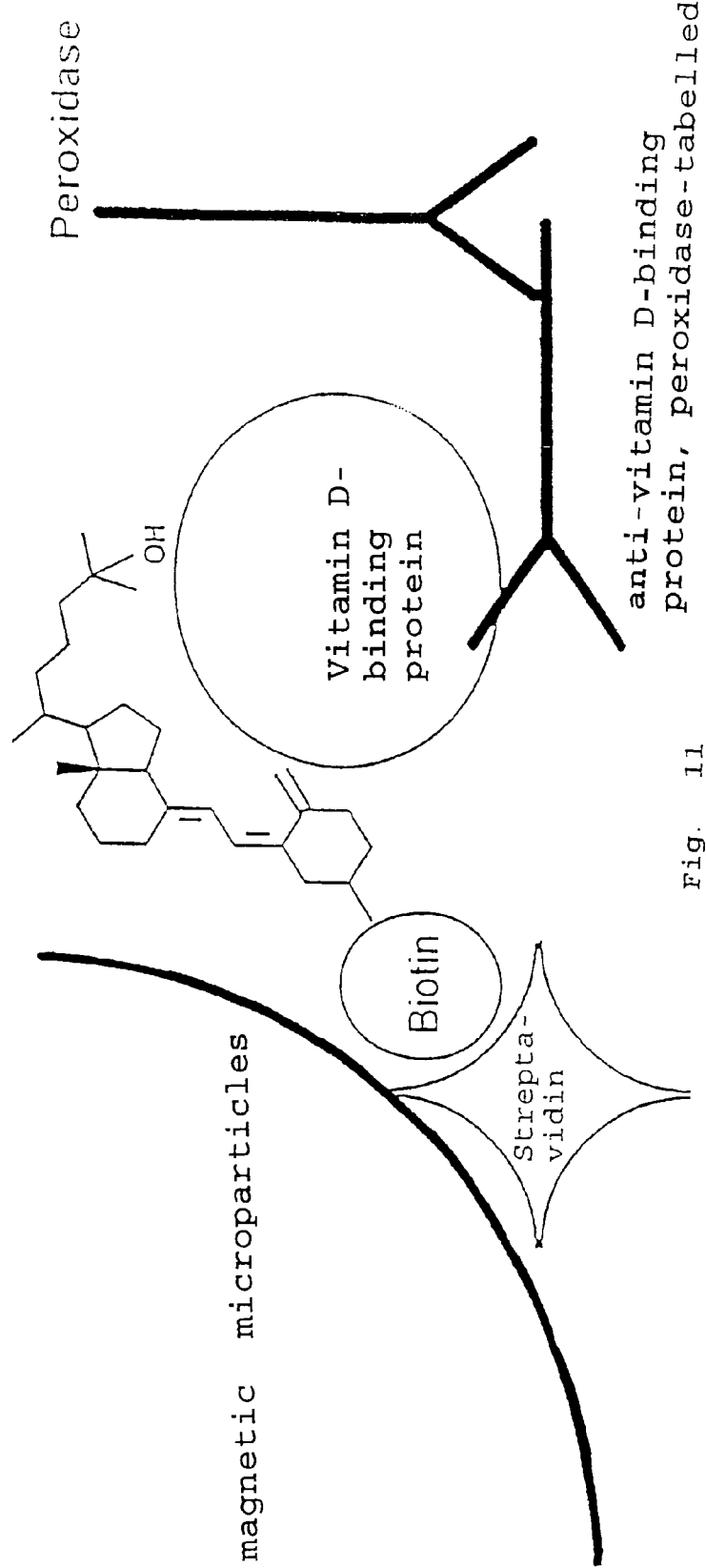
FIGS. 11 and 12 schematic representations of competitive ELISAs with the employment of microparticles.

FIG. 11 shows the schematic representation of a competitive ELISA employing microparticles. Here, 25-OH-vitamin D-biotin is bound to microparticles via streptavidin. 25-OH-vitamin D derivative is then bound thereto. Vitamin D binding protein and the sample concerned are then added in liquid phase. Binding proteins and 25-OH-vitamin $D_3$ from a standard or a sample compete for the binding site of the conjugate. The bound components are separated in that they are held back via the microparticles by a magnet, whereas the remainder with the non-bound substances is removed. The quantity of coupled binding protein is determined in a 2-stage process with a primary antibody against vitamin D binding protein and a secondary peroxidase-labelled antibody.

Figure 12:
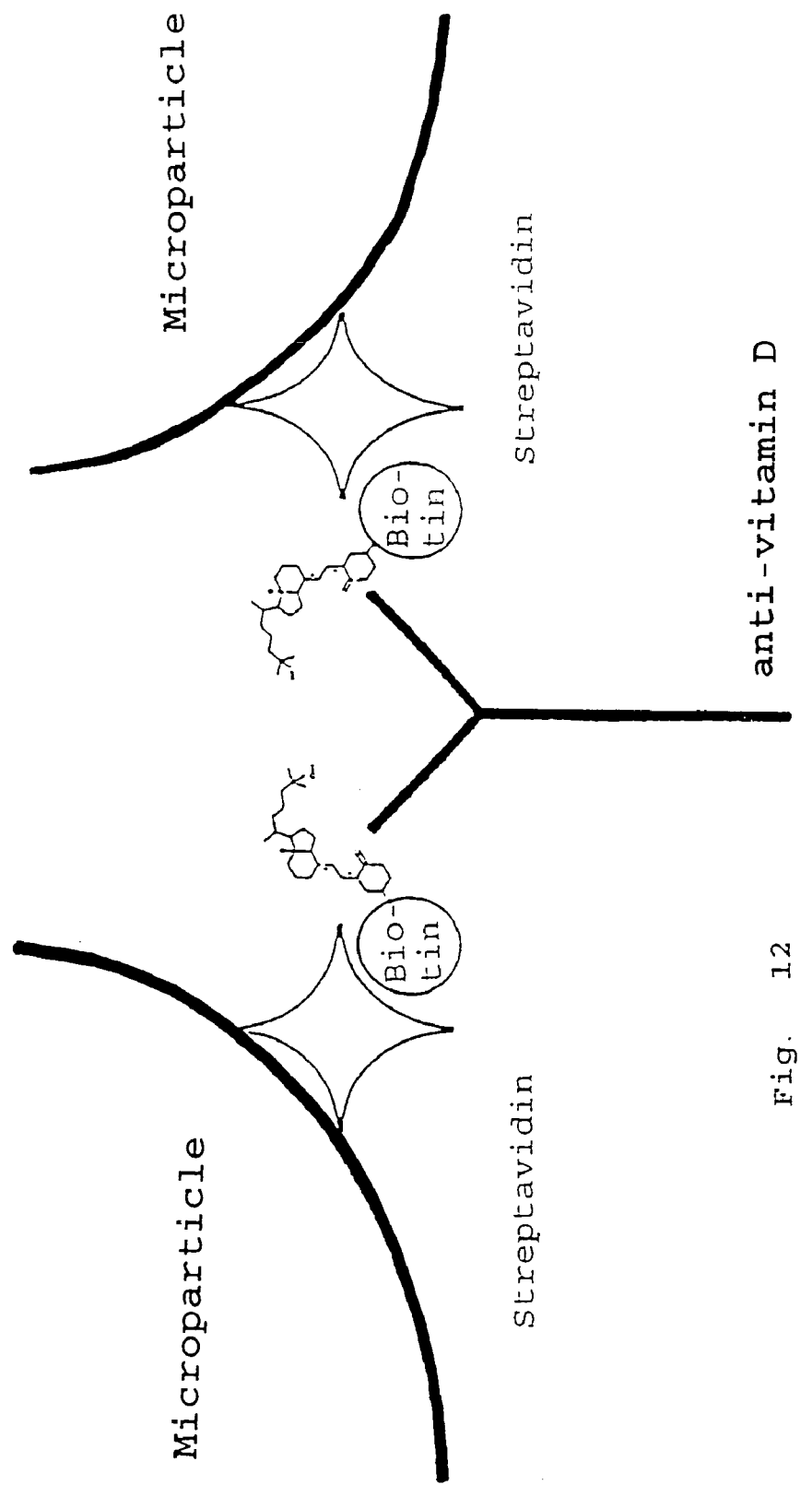

FIG. 12 shows a schematic representation of a competitive ELISA employing microparticles. 25-OH-vitamin-D-biotin is bound to microparticles via streptavidin. Then the liquid sample with 25-OH-vitamin $D_3$ (from a standard or a sample) is added, as is a non-saturating quantity of antibodies. The conjugate and the native vitamin $D_3$ compete for the binding of the antibody. The quantity of bound antibodies is effected by means of agglutination of the microparticles. This can be determined for example directly by means of nephelometric analysis or turbimetric analysis.

Figure 13:
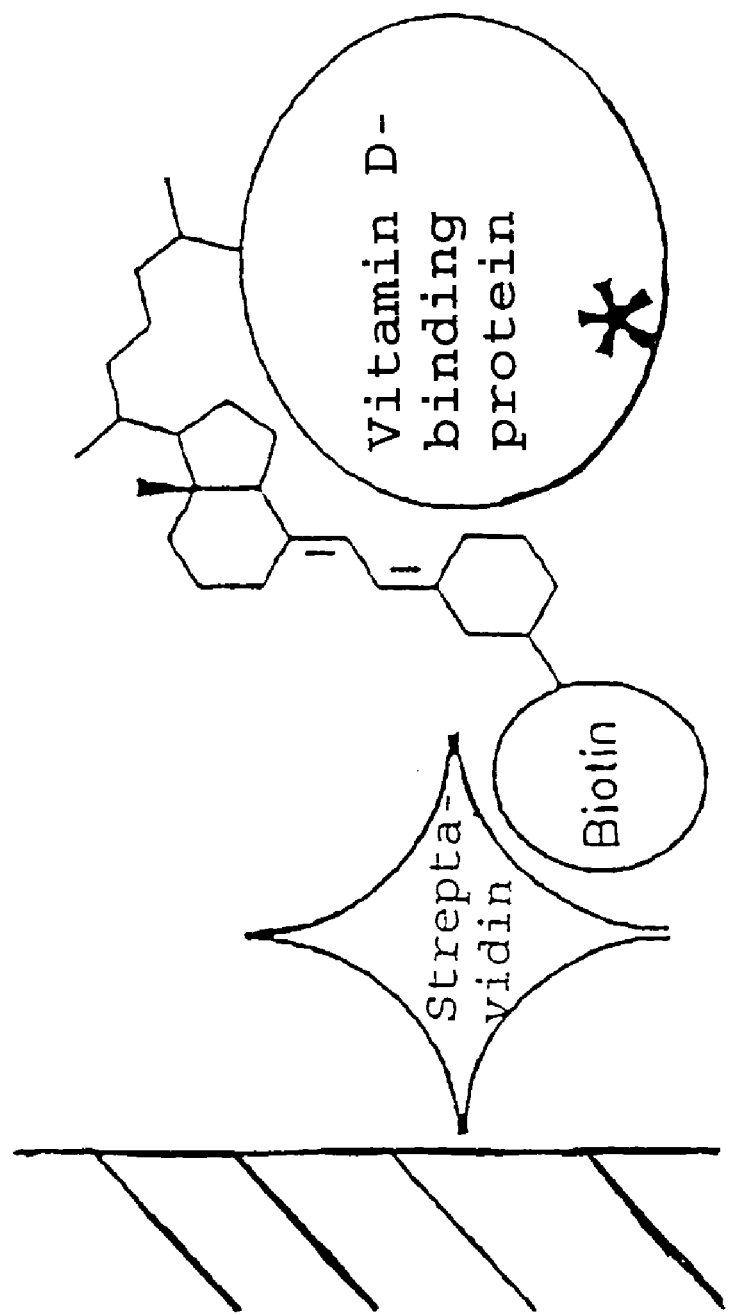
FIG. 13 schematic representations of a competitive binding assay for 25-OH-vitamin D employing a 25-OH-vitamin D conjugate in accordance with the invention and a directly labelled vitamin D binding protein.

FIG. 13 shows the scheme of a competitive binding assay, whereby the vitamin D binding protein is directly labelled, for example radioactively with $^{125}$Iodine, or for an electrochemoluminescence, with ruthenium(II)tris-(bipyridine)-NHS-ester. The marking may also be enzymes such as peroxidase, alkaline phosphatase, β-galactosidase, etc., or may also be FITC.

Figure 14:
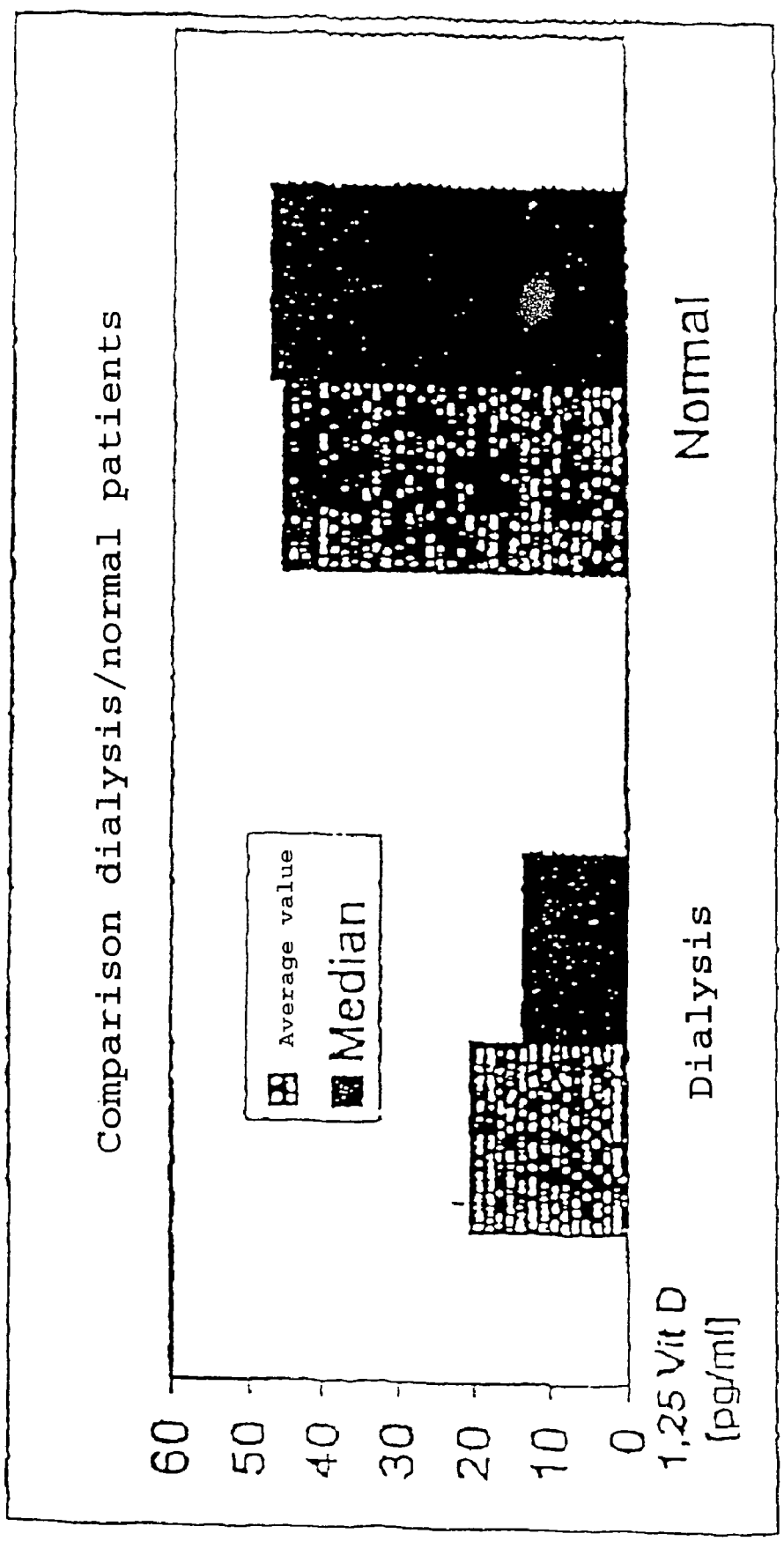
FIG. 14 a block diagram of the comparison of the 1,25-dihydroxy vitamin D-content in serum from dialysis patients and normal patients.

FIG. 14 illustrates in a block diagram the different 1,25-dihydroxy vitamin D contents in serum from dialysis patients and from normal patients.

Figure 15:
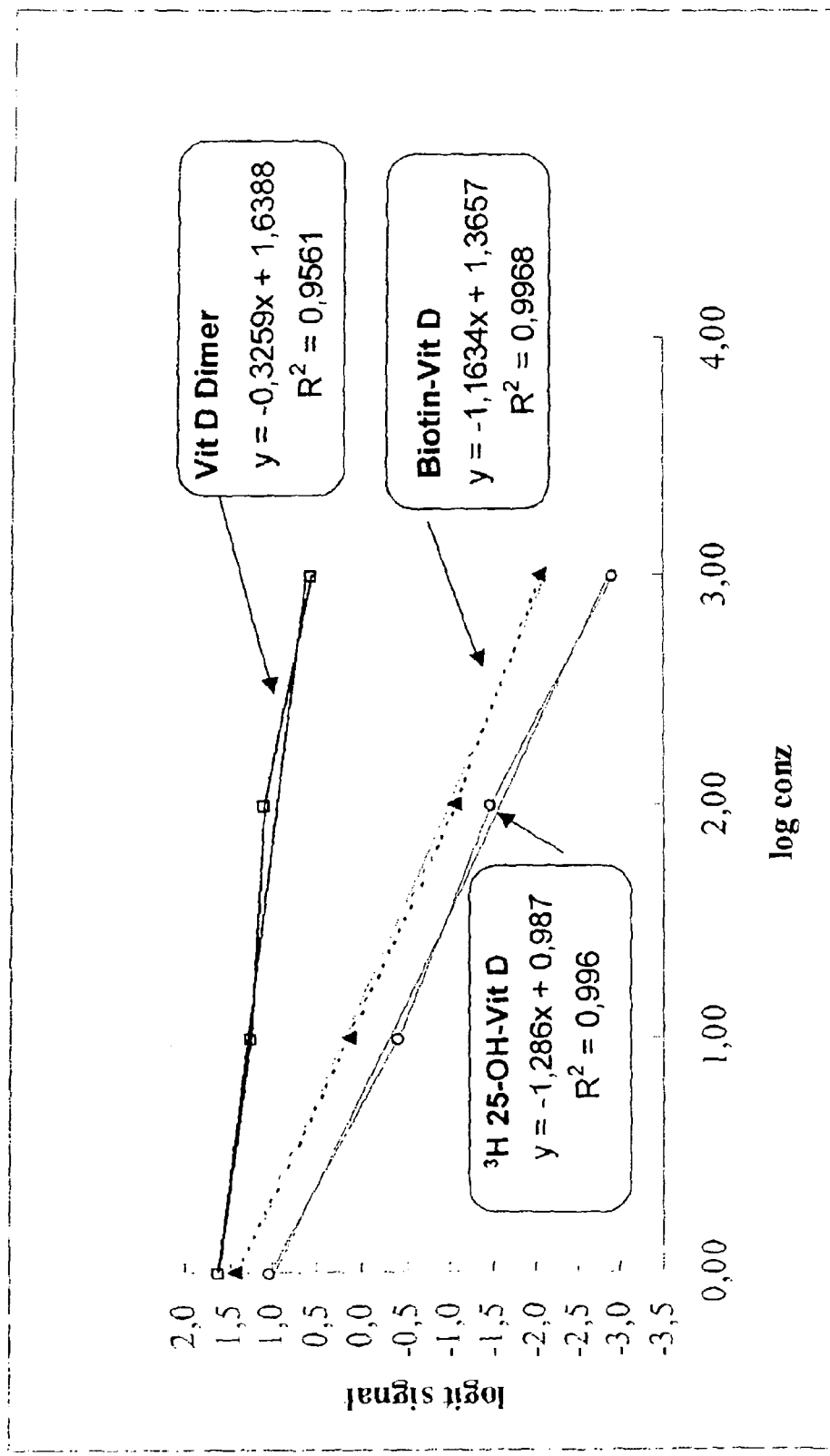
FIG. 15 Scatchard plots of the displacement efficiencies of biotinylated 25-hydroxy vitamin D as claimed in claim 1, a vitamin D dimer and $^3$H-25-OH-vitamin D on vitamin D binding protein DBP from goat serum.

FIG. 15 shows Scatchard plots of the biotinylated 25-hydroxy vitamin D as claimed in claim 1, a 25-hydroxy vitamin D dimer obtained by a reaction with succinic anhydride and $^3$H-25-OH-vitamin D on vitamin D binding protein from goat serum. As can be seen from the Scatchard plots, the displacement efficiencies of the compounds of the present invention were all close to 1, whereas compound C in WO 97/24127 (Holick et al.) could only displace the tritiated compound from human vitamin D binding protein when it was present in an eleven-fold excess. Moreover, the Scatchard plots show that the displacement efficiencies were linear and parallel over the relevant concentration ranges.

The known detection methods for proteins such as the competitive ELISA are based on the principle that the compound to be detected competes with a binding protein or conjugate for a binding site. Then, the quantity of bound binding protein or conjugate is determined and on the basis of a calibration curve the concentration of the compound to be detected is determined.

The test principles shown in the Figures can be carried over simply to other vitamin D derivatives. 1α,25-dihydroxy vitamin $D_2$ and $D_3$ are to be particularly mentioned. In this case a binding protein or a receptor or antibody must be selected which specifically recognises the 1α,25-dihydroxy vitamin D analog. The associated bifunctional 1α,25-dihydroxy derivative can be obtained enzymatically by means of reaction of 25-OH-vitamin D-3β-cyanoethylether with 25-OH-vitamin-D-1α-hydroxylase, reduction to the amine and finally the addition of the second functional group. Further, derivatives of vitamin $D_2$ and vitamin $D_3$ are here proposed. The synthesis thereof can be effected through the route set out in Example 1.

EXAMPLES

Example 1

Synthesis of 25-OH-Vit.-$D_3$-3β-3'[6-N-(biotinyl)-hexamido]amidopropylether (4)

All reactions were performed in the dark in a dry nitrogen atmosphere. Intermediate products were stored at −20EC. HPLC-pure solvents were employed. The 25-OH-vitamin $D_3$ was obtained from BIOMOL Feinchemikalien GmbH, Hamburg, the LC-BHNS (Long-Chain-Biotinyl-N-ϵ-amino caproyl-hydroxy-succinimide ester) from Sigma Chemie, and all further chemicals from Fluka, Darmstadt. The mass spectroscopy (FAB) was carried out with a Finigan-MAT-90, the NMR-measurements with a Bruker-ARX-400 (400 MHz) or a Bruker-ARC-250F (250 MHz).

(i) 25-OH-Vitamin $D_3$-3β-cyanoethylether (2)

5 mg 25-OH-vitamin $D_3$ (12.5 µMol), dissolved in methylene chloride ($CH_2Cl_2$), was transferred into a vial filled with nitrogen and the solvent was distilled off. The solid remainder was dissolved in 1 ml acetonitrile and mixed with 10 drops of a mixture of tertiary butanol and acetonitrile (9:1 v/v) and 130 µMol acrylonitrile (10 eq.) in 100 µl acetonitrile [stock solution: 86 µl acrylonitrile (1.3 mMol) diluted with acetonitrile to 1 ml]. The clear solution was stirred for 15 minutes at 6EC. 6.25 µMol potassium hydride (0.5 eq.) in 25 µl tertiary butanol/-acetonitrile (9:1 v/v) [stock solution: 10 mg KH (250 µMol) in 1 ml tertiary butanol/acetonitrile (9:1 v/v)] was added. The flocculation thereby arising dissolved again immediately. The mixture was stirred at 6EC. Repeated thin layer chromatography (DC) of individual samples with 20% petrolether in methyl-tert.-butylether (MTBE) on silica gel showed that after 10 minutes 90% of the initial compound had been reacted. After 15 minutes a few drops of the reaction mixture were prepared with about 5 drops of water and 0.5 ml MTBE. The thin film chromatography of the organic phase showed no further educt. After 40 minutes the entire reaction mixture was prepared with water/MTBE. 4 mg oleaginous product was obtained.

| IR (NaCl/CH$_2$Cl$_2$): | 3422 | OH |
|---|---|---|
| | 2941, 2872 | CH |
| | 2252 | nitrile |
| | 1105 | ether |

The HPLC-analysis (3% MeOH/CH$_2$Cl$_2$) showed 93% product and 7% educt. Thus, 4 mg product contained 3.7 mg (8.2 µMol) target compound, which corresponds to a yield of 74%.

(ii) 25-OH-vitamin D$_3$-3β-3'amino propylether (3)

3.75 mg (8.3 µMol) nitrile from (i) was dissolved in 2 ml ether, to which was added 125 µMol lithium hydride dissolved in 1 ml ether (stock solution: 7 mg fresh finely powdered LiH in 7 ml ether) and stirred for 1 hour at room temperature in a nitrogen atmosphere. 169 µMol LiAlH$_4$ was added as suspension in 1 ml ether (base: 18 mg fresh finely powdered LiAlH$_4$ in 3 ml ether). After a further hour the mixture was prepared with 1 ml concentrated KOH, 5 ml H$_2$O and 4×20 ml MTBE. The thin film chromatography of a sample with 1:1 MTBE/petrolether on silica gel showed only the starting point. The diole was at R$_f$ 0.27; the nitrile at R$_f$ 0.4. The substance obtained was processed further without further analysis and purification.

(iii) 25-Hydroxy vitamin D$_3$-3β-3'[6-N-(biotinyl)hexamido]-amidopropylether (4)

3 mg (6.6 µMol) 25-OH-vitamin D$_3$-3β-amino propylether (3) from (ii) was dissolved in 1 ml dimethylformamide (DMF). Then, in a nitrogen atmosphere, 3 mg (6.6 µMol) LC-BNHS and 1 µl (17.5 µMol) triethylamine were added. Stirring for 18 hours at room temperature took place, the DMF was distilled off and the residue pre-purified with 20% methanol (MeOH) in CH$_2$Cl$_2$. 12 mg (>100%) of the substance so obtained was purified by means of HPLC (conditions: Knauer Kromasil-100, 5 µM, 250×4 mm, 10% MeOH in CH$_2$Cl$_2$, 1.5 ml/min, OD 265 nm, 7 minutes). The yield amounted 1.2 mg (1.5 µMol). This corresponds to 12% referred to the 25-OH-vitamin D$_3$ and 18% referred to the nitrile compound.

TABLE I

Biotin-25-OH-Vitamin D$_3$

| H | Mult | Cc [Hz] | Assignment |
|---|---|---|---|
| 6.42 | 1 | Dd | 5.7 | NH (Biotin) |
| 6.2 | 1 | D | 11 | 6 |
| 6.0 | 1 | D | 11 | 7 |
| 5.85 | 1 | Dd | 5.7 | NH (Biotin) |
| 5.55 | 2 | M | | 3-O—CH$_2$(28) |
| 5.38 | 1 | S | | NH or OH |
| 5.05 | 1 | D | 2 | 19 |
| 4.83 | 1 | D | 2 | 19 |
| 4.77 | 1 | S | | NH or OH |
| 4.51 | 1 | M | | HC—NH I Biotin |
| 4.33 | 1 | M | | HC—NH II Biotin |
| 3.53 | 1 | M | | 3 |
| 2.53 | 1 | D | 10 | 4 |
| 1.21 | 6 | S | | 26,27-CH$_3$ |
| 0.93 | 3 | D | 6 | 21-CH$_3$ |
| 0.54 | 3 | S | | 18-CH$_3$ |

MS (Finigan MAT 90); (FAB): 797 (MH$^+$) of 5.9.97 and 28.11.97; $^1$H-NMR (Bruker ARX 400) in CDCl$_3$/TMS at 400 MHz.
The data of the analysis are shown in table I.

Example 2

Stability of 25-OH-Vit.-D$_3$-3β-3'[6-N-(biotinyl)-hexamido]amidopropylether

In each case 20 mg purified 25-OH-D$_3$-biotin compound (25-OH-vitamin D$_3$-3β-3'[6-N-(biotinyl)-hexamido]amidopropylether) from Example 1 was placed in an NMR test tube to which 1 ml solvent was added. The solvent was a mixture of deuterium chloroform:deuterium acetonitrile:D$_2$O in the ratio 3:2:1 with a pH-value between 4 and 5. The samples were stored for 200 days under the conditions set out below and the NMR spectra were investigated at regular intervals.
Sample 1: light excluded at −20EC;
Sample 2 light excluded at +4−6EC;
Sample 3: light excluded at room temperature;
Sample 4: subject to strong light (on a window ledge) at room temperature.

Samples 1 and 2 showed no substantial alteration in NMR-spectrum over the entire time. An HPLC analysis confirmed that samples 1 and 2 were intact even after 200 days in protonic solvent. Sample 3 showed a minimal alteration of NMR spectrum after 100 days. The HPLC analysis indicated that more than 78% of the compound was still intact. Sample 4 was degraded after two months. The investigation of stability shows that the compound is very stable when light is excluded, even in protonic solvent and without cooling.

Example 3

25-Hydroxy vitamin D-ELISA with 25-Hydroxy vitamin D$_3$-3β-3'[6-N-(biotinyl)-hexamido] amidopropylether The detection was effected in accordance with the principle illustrated in FIG. 2. For this purpose, 25-OH-vitamin D-3β-3'[6-N-(biotinyl)hexamido] amidopropylether had to be bound to a solid phase via streptavidin.
(i) Coating a Microtitration Plate with Streptavidin Into each of the wells of a microtitration plate there was placed 100 ng streptavidin, dissolved in 200 µl 60 nM NaHCO$_3$, pH 9.6, and the plate incubated overnight at 4EC. The streptavidin solution in the well was removed and each well washed five times with 200 µl washing buffer (PBS, pH 7.4 with 0.05% Tween-20). Then, 250 µl assay buffer was placed in each well. For the assay buffer, 5 g casein was dissolved in 100 ml 0.1 N NaOH and topped up with PBS, pH 7.4 to 1 L volume. The solution was boiled for one hour, the volume supplemented to 1 litre with distilled water, the pH value set to 7.4 and 0.1 g thimerosal added to avoid growth of microbes. The wells in the microtitration plate were incubated for 1 hour at room temperature with assay buffer, then the assay buffer was removed and each well washed five times with in each case 200 µl washing buffer.

(ii) Binding of 25-Hydroxy vitamin $D_3$-3β-3'[6-N-(biotinyl)-hexamido]amidopropylether Into each well there was introduced 100 µl biotin-vitamin D-solution (10 ng 25-OH-vitamin D-3β-3'[6-N-(biotinyl) hexamido]amidopropylether in 100 µl washing buffer) and incubated for one hour at room temperature, in the dark whilst being shaken. Then, the biotin-vitamin D-solution was removed from the wells and each well washed five times in each case with 200 µl washing buffer. In the liquid phase, there was effected a competitive binding of vitamin D binding protein in the presence of 25-OH-vitamin D from a standard or a sample.

(iii) Sample Preparation

50 µl serum was mixed by vortexing with 200 µl ethanol$_{abs}$ (pre-cooled to −20EC) in a 1.5 ml Eppendorf reaction vessel and precipitated for 20 minutes at −20EC. The samples were centrifuged at maximum speed of rotation in an Eppendorf table centrifuge and the result removed and placed in the ELISA.

One can as a rule assume that plasma or serum samples are stable for about two weeks at 4EC. In the case of longer storage they must be deep frozen until they are analysed. Before storage, urine samples must be set to a pH-value between 6 and 8 with 1 N NaOH. Then, they may be stored at 4EC for about 14 days; in the case of longer storage these also must be deep frozen until the analysis is carried out.

(iv) Competitive Binding

In each case 100 µl vitamin D binding protein, isolated from goat serum (1:15000 in assay buffer with 3% (w/v) PEG 6000) together with 10 µl standard, control or sample (10 µl result from the sample preparation) was placed in the wells. The microtitration plate was incubated for 24 hours at 4EC in the dark and subject to shaking. Then, the solution was removed from the wells and the wells washed five times in each case with 200 µl washing buffer.

(v) Detection of the Competitive Binding

In each case 100 µl rabbit-anti-vitamin D-binding-protein (1:10000 diluted in assay buffer having 3% (w/v) PEG 6000) was introduced into the wells and incubated for 1 hour in the dark and subject to shaking, at room temperature. The solutions were removed from the wells and each well washed five times with in each case 200 µl washing buffer. The quantitative determination was effected with 100 µl anti-rabbit-IgG-peroxidase (1:20000 diluted in washing buffer). Incubation took place for 1 hour at room temperature. Thereafter antibody solutions were taken off and each well washed five times in each case with 200 µl washing buffer. For the colour reaction 100 µl tetramethylbenzidine(TMB) substrate solution (ready for use, from NOVUM Diagnostika GmbH, Dietzenbach, Germany) was introduced into the wells. After 30 minutes the colour development was stopped by the addition of 50 µl 2 M $H_2SO_4$ per well. The measurement of the optical density was effected at 450 nm. The following tables II and III show the pipetting scheme for the microtitration plate and the values for the optical density.

As standards there were employed solutions of 25-OH-vitamin $D_3$ in assay buffer with the following concentrations: 0, 8, 20, 50, 125 and 312 nMol/L (see calibration curve in FIG. 5A). As controls or samples there served four serums from patients having a D-hypovitaminosis (sample nos. 24, 203, 963, 965) and four randomly chosen normal serums (sample nos. NP 18, NP 25, NP 34, NP 37-test series 3 and 4). For the vitamin D-deficiency serums additionally the 25-OH-vitamin D concentration was determined by means of competitive binding assay with the aid of $^3$H-25-OH-vitamin D. As a further "controls" there served four solutions for which the respective concentrations of 25-OH-vitamin D were known from other determinations, either from manufacturer information or by means of a competitive binding assay (CBPA) with $^3$H-25-OH-vitamin D.

TABLE II

| | | SAMPLE ARRANGEMENT | | | | |
|---|---|---|---|---|---|---|
| Pipetting Scheme | Standard nMol/L | Duplicate value of column 1 | Serum sample No. | Duplicate value of column 3 | Controls | Duplicate value of column 5 |
| | | | Column | | | |
| Row | 1 | 2 | 3 | 4 | 5 | 6 |
| A | NSB | NSB | 24 | 24 | K1 (CPBA) | K1 (CPBA) |
| B | 0 | 0 | 203 | 203 | K2 (CPBA) | K2 (CPBA) |
| C | 8 | 8 | 963 | 963 | K3 (HPLC) | K3 (HPLC) |
| D | 20 | 20 | 965 | 965 | K4 (HPLC) | K4 (HPLC) |
| E | 50 | 50 | NP 18 | NP 18 | | |
| F | 125 | 125 | NP 25 | NP 25 | | |
| G | 312 | 312 | NP 34 | NP 34 | | |
| H | | | NP 37 | NP 37 | | |

NSB: Non-specific binding buffer (Assay buffer without Vitamin D binding protein)

TABLE III

MEASUREMENT VALUES AFTER 30 MINUTES COLOUR DEVELOPMENT

| OD 450 nm | Standard | Duplicate value for column 1 | Serum sample No. Column | Duplicate value for column 3 | Controls | Duplicate value for column 5 |
|---|---|---|---|---|---|---|
| Row | 1 | 2 | 3 | 4 | 5 | 6 |
| A | — | — | 0.947 | 1.023 | 1.903 | 2.300 |
| B | 2.256 | 2.182 | 0.853 | 0.910 | 0.393 | 0.371 |
| C | 1.845 | 1.861 | 0.646 | 0.637 | 1.674 | 1.586 |
| D | 1.432 | 1.456 | 1.429 | 1.303 | 0.578 | 0.634 |
| E | 0.625 | 0.612 | 0.524 | 0.547 | | |
| F | 0.287 | 0.261 | 0.454 | 0.419 | | |
| G | 0.156 | 0.176 | 0.341 | 0.368 | | |
| H | — | — | 0.421 | 0.386 | | |
| $B_{max}$ | 2.801 | 2.676 | | | | |

From the mean values of columns 1 and 2 and the known concentration of 25-OH-vitamin D, the calibration curve shown in FIG. 5A was produced. The ordinate shows the optical density as mean value of the two measurements at 450 nm; the abscissa shows the concentration of 25-OH-vitamin D in nMol/l. The results are summarised in Table V.

Example 4

Comparative Binding Analysis with $^3$H-25-OH-vitamin D as Competitive Partner Insofar as no other indication is given, all reagents, buffers and materials were the same as in above-mentioned Example 3. There served as competitive binding partner (tracer) tritium-labelled 25-OH-vitamin $D_3$. Differing from Example 3, the measurement samples were purified by means of extraction (into individual values). For this purpose, in each case 50 µl sample [non-specific assay buffer NSB, standard, control, patients sample (plasma, serum or urine)] was introduced into a 1.5 ml disposable reaction container, 200 µl acetonitrile added, mixed, the container walls centrifuged free, and the mixture incubated for 20 to 30 minutes at 4EC. The mixture was centrifuged at 1700×g for 10 minutes. The determinations were effected with the results using duplicate values.

For this purpose 25 µl clear result was transferred to a glass test tube (or into a special-RIA-container from Sarstedt, Darmstadt) and 10 µl tracer (3H-25-OH-D), 300 µl assay buffer and 100 µl vitamin D-binding protein (not in NSB) added. The test tube contents were mixed, incubated for one hour at 4EC and, to remove non-bound radioactive tracer, 100 µl activated charcoal suspension (activated charcoal containing phosphate buffer with 0.1% $NaN_3$) was added. The test tube content was mixed, incubated for 3 to 5 minutes at 4EC, and the active charcoal pelletized by means of centrifuging for 10 minutes at 1700×g. Then, in each case 400 µl of the result was transferred to a counter container (7 ml) and, after the addition of 2 ml scintillator liquid such as Aquasafe™ 300 or HiSafe™ III, the radioactivity present in the result was counted (2 minutes in a beta-counter). The measurement value for the controls, after production of the calibration curve, are shown in Table V.

The comparison with the ELISA according to Example 3 shows that for both assay procedures (ELISA and CBPA) it is the case that the normal range for 25-OH-vitamin D in plasma or serum is about 25-125 nmol/l. The sensitivity limit of the test systems was determined as $B_0$+2SD. It amounts to about 2.5 nmol/l.

Cross reactions: To serum treated with activated charcoal there was added 25-OH-vitamin $D_2$ (125 nmol/l), 24,25-$(OH)_2$-vitamin $D_3$(250 nmol/l) and 1,25-$(OH)_2$-vitamin $D_3$ (250 nmol/l). The 25-OH-vitamin $D_2$ cross-reacted to 60%, the 24,25-$(OH)_2$-vitamin $D_3$ cross-reacted to 100%, whereas the 1,25-$(OH)_2$-vitamin $D_3$ show no cross-reactivity. Similar results have been found or expected also for multifunctional 25-OH-vitamin D conjugate in accordance with the invention.

Reproducibility: In repeat measurements (n=11) of a sample containing 25-dihydroxy vitamin $D_3$ the following results were achieved. Similar applies also for measurements with the aid of the multifunctional 25-OH-vitamin D conjugate in accordance with the invention:

TABLE IV

| | Number | Mean value nmol/l | Variance % |
|---|---|---|---|
| Intra-assay variance: | | | |
| Sample 1 | 32 | 11.3 | 12.5 |
| Sample 2 | 32 | 318 | 7.2 |
| Inter-assay variance: | | | |
| Sample 1 | 9 | 9.9 | 17 |
| Sample 2 | 9 | 310 | 11 |
| Clinical: | | | |
| | Number | Mean value nmol/l | |
| Normal persons | 35 | 54 | |
| Patients having hip joint fractures | 43 | 9.5 | |

For the samples mentioned in Example 3 the following 25-OH-vitamin D concentrations were determined with the methods according to Examples 3 and 4.

TABLE V

| Serum sample No. | ELISA with 25-OH-D-Biotin nMol/L | CBPA with $^3$H-25-OH-D nMol/L | Controls | ELISA with 25-OH-D-Biotin nMol/L | Alternative determination nMol/L |
|---|---|---|---|---|---|
| 24 | 32.9 | 33.3 | K1 | Not measured | 20 (a) |
| 203 | 36.8 | 29.19 | K2 | 76.8 | 75-125 (a) |
| 963 | 48.9 | 38.4 | K3 | 15.0 | 20-33 (b) |
| 965 | 21.8 | 15.8 | K4 | 51.3 | 72-120 (b) |
| NP 18 | 57.0 | | | | |
| NP 25 | 67.9 | | | | |
| NP 34 | 82.4 | | | | |
| NP 37 | 72.9 | | | | |

(a) CBPA with $^3$H-25-OH-D
(b) Manufacturer information

The values indicated by the manufacturers were in general higher that the concentrations determined in the competitive binding assay. This suggests that in the supplied samples a significant part of the 25-OH-vitamin D had already decayed or transformed through the action of light.

Example 5

Checking of the ELISA-Determination by Means of HLPC

Thus, for various samples the 25-OH-vitamin D concentration was determined by means of the ELISA according to Example 3 and, for the purpose of checking, by means of HPLC. For the calibration curve, standards were employed having vitamin $D_3$ concentrations of 0, 8, 20, 50, 125 and 312 nMol/l. All samples and standards were measured with duplicate values. The 25-OH-vitamin $D_3$-concentration of the samples was then determined on the basis of the calibration curve from the mean of the duplicate values.

The results are shown in the following table VI.

TABLE VI

| | 25-OH-Vitamin $D_3$ (nMol/L) | |
|---|---|---|
| Sample | HPLC | ELISA |
| 1 | 20-33 | 30 |
| 2 | 72-120 | 76 |
| 3 | 79-102 | 96 |
| 4 | <15 | <Sensitivity limit |
| 5 | <15 | 7.4 |

Example 6

Long Term Stability of 25-Hydroxy Vitamin D-Conjugate in the ELISA Detection

Calibration curves were repeated with the same standard solutions and reagents according to Example 3, after 60 and 100 days, in order to determine to what extent an ELISA detection using the biotin-25-OH-vitamin D-conjugate in accordance with the invention changed with the passage of time, when the reagents were stored in the interim at 4 to 6EC in the dark. The table below shows the respective optical densities after 30 minutes development (see Example 3).

TABLE VII

| Standard | Duplicate value for column 1 | After 60 Days | Duplicate value for column 3 | After 100 Days | Duplicate value for Column 5 |
|---|---|---|---|---|---|
| | | | nMol/L | | |
| Standard | 1 | 2 | 3 | 4 | 5 | 6 |
| NSB | — | — | 0.191 | 0.280 | 0.088 | 0.109 |
| 0 | 2.256 | 2.182 | 2.227 | 2.285 | 1.471 | 1.562 |
| 8 | 1.845 | 1.861 | 2.041 | 2.125 | 1.345 | 1.366 |
| 20 | 1.432 | 1.456 | 1.860 | 1.903 | 1.079 | 1.060 |
| 50 | 0.625 | 0.612 | 1.293 | 1.214 | 0.610 | 0.690 |
| 125 | 0.287 | 0.261 | 0.606 | 0.615 | 0.442 | 0.329 |
| 312 | 0.156 | 0.176 | 0.448 | 0.434 | 0.293 | 0.257 |

If the values of the various calibration curves, deducting the respective non-specific binding, are presented in a diagram (see FIG. 5B) it can readily be seen that the calibration curves have the same shape apart from a relative vertical displacement. This shows that the sensitivity and specificity of the ELISA test had not changed over the above-mentioned period of time.

Example 7

25(OH)-vitamin $D_3$-ELISA-MTP with Anti-Vitamin-D-Binding Protein

The trial was effected in substance in accordance with the protocol of Example 3 and with the principle illustrated in FIG. 4. The following buffers were employed:
  a) washing buffer: PBS, pH 7.4 with 0.05% Tween-20; b) assay buffer: 5 g casein was dissolved in 100 ml 0.1 N NaOH and supplemented with PBS, pH 7.4 to 11. Then 3% (w/v) PEG-6000 and 0.1 g Thimerosal™ were added. All incubations were effected in the dark and subject to shaking.
(i) Coating the Microtitration Plate
  Into the wells of a microtitration plate there were introduced in each case 100 µl rabbit-anti-vitamin D-binding protein in 60 mM $NaHCO_3$, pH 9.6, and the plate incubated overnight at 4EC. The solutions were removed and each well washed five times with 200 µl washing buffer. Then, 250 µl assay buffer was introduced into each well and the plate incubated for 1 hour at room temperature. The assay buffer was removed and each well was washed five times with in each case 200 µl washing buffer.
(ii) Sample Preparation
  50 µl serum, plasma or standard was mixed in a 1.5 ml Eppendorf reaction container with 200 µl ethanol$^{abs}$ (pre-cooled to −20EC), vortexed and then precipitated for 20 minutes at −20EC. The samples were centrifuged in an Eppendorf table centrifuge at maximum rotations. The result was taken and employed in the ELISA.

(iii) ELISA

Firstly, into each individual well 100 μl vitamin D-binding protein, diluted in assay buffer, was introduced and incubated for 1 hour at room temperature. The plate was then knocked out and each individual well washed five times in each case with 200 μl washing buffer.

Thereafter, there was introduced into the wells in each case 100 μl biotin-vitamin D, diluted in assay buffer, together with 10 μl standard, sample or control. The plate was incubated for 24 hours at 4EC. The solutions were again removed and each well washed five times in each case with 200 μl washing buffer.

As a third step there was introduced into the wells in each case 100 μl peroxidase-coupled streptavidin in a 1:10000-dilution in washing buffer, and incubated for 45 minutes at room temperature. The plate was knocked out and each well washed five times in each case with 200 μl washing buffer.

For the colour reaction, there was introduced into each well 100 μl TMB-substrate solution. After sufficient colour development (30 minutes) the reaction was stopped with 50 μl 2M $H_2SO_4$ per well. The measurement of the optical density was defected at 450 nm. Similar to same results were obtained as in Example 3 or table V.

Example 8

Content of a Test Pack or a Reagent Set for the Detection of 25-hydroxy Vitamin D and 1α,25-dihydroxy Vitamin D Content of the test pack or test reagents and their preparation:

Standards, for example 6 vials of 25-OH-vitamin D standards with the concentrations 0, 8, 20, 50, 125 and 312 nmol/l; ready for use in washing buffer.

Microtitration plates, for example coated with streptavidin, sterile packed and pre-washed.

Buffer solutions, for example washing buffer, NSB-buffer and assay buffer, stopper solution.

Controls, for example 2 vials 25-OH-vitamin D controls in human serum. Control 1 (30 nmol 25-OH-D/L), control 2 (80 nMol 25-OH-D/L).

Tracer, for example a vial with biotin-vitamin D (25-OH-vitamin $D_3$-3β-3'[6-N-(biotinyl)-hexamido]amidopropylether) in washing buffer (100 ng/ml).

Vitamin D-binding protein, for example a vial with binding protein from goat serum in phosphate buffer with 0.1% $NaN_3$ as stabilising agent.

Marker, for example a vial of anti-rabbit-IgG-peroxidase in washing buffer.

TMB-developer-solution, for example a vial of stabilised tetramethylbenzidine-developer solution in washing buffer.

Example 9

ELISA for the Quantitative Detection of 1,25-dihydroxy Vitamin D

The detection of 1,25-vitamin $D_3$ was effected in accordance with the principle illustrated in FIG. 2, except that 1,25-dihydroxy vitamin $D_3$-biotin compound served as tracer. In the competition, 1,25-dihydroxy vitamin $D_3$ from a standard or a sample, together with a 1,25-dihydroxy vitamin D binding protein, a monoclonal mouse-anti-1α,25-dihydroxy vitamin D-antibody (B. Mawer et al. in Steriods, 1985, 46, 741-754), were brought together. The 1,25-dihydroxy vitamin $D_3$ from a standard or a sample and the immobilised 1,25-dihydroxy vitamin $D_3$-biotin compound then compete for the binding site of the antibody. The detection is effected by means of peroxidase-labelled antibodies (goat-anti-mouse-IgG-POX).

(i) The coating of the microtitration plate with streptavidin was effected as in Example 3, whereby however the washing buffer contained 0.1% Triton X-100 as a detergent. Otherwise than as in example 3, the wells in the microtitration plate were no longer washed with washing buffer after the treatment with streptavidin solution, but in each case treated for 1 hour with 250 μl aqueous sorbitol solution (Karion™ F 1:4 in water). The binding of the tracer (1,25-dihydroxy vitamin D-biotin) was effected as in Example 3, except that there was introduced into each well 200 μl tracer solution (20 ng 1,25-dihydroxy vitamin $D_3$-3β-3'[6-N-(biotinyl)-hexamido]amidopropylether in washing buffer). The 1,25-dihydroxy vitamin D-biotin was synthesised as schematically illustrated in FIG. 1, except that after the first step the excess 3-cyanoethylated 1-OH-vitamin D intermediate compound was isolated. There can however, also be isolated as desired one of the following intermediate compounds or, after a mixed synthesis, specifically the 1,25-dihydroxy vitamin $D_3$-3β-3'[6-N-(biotinyl)-hexamido]amidopropylether by means of HPLC.

(ii) Since in human serum the ratio of 25-OH-vitamin $D_3$ to 1,25-dihydroxy vitamin $D_3$ as rule is in the range of 1000:1 the quantitative detection of 1,25-dihydroxy vitamin D requires a thorough preparation of the samples by means of a combined distribution and absorption chromatography. In the first step, for this purpose, Extrelut™ Kieselguhr columns (Merck, Darmstadt) are brought to equilibrium each with 500 μl tris-buffer and then there is applied to the columns in each case 500 μl of a standard, control or investigation sample—in duplicates; the samples can then draw into the columns for 10 minutes. The separation of the vitamin D-compounds from the Extrelut™ columns was effected by means of four times 1 ml diisopropylether at intervals in each case of 3 minutes. The Extrelut™ extract was directly transferred to a silica cartridge (Merck, Darmstadt) and the Extrelut™ columns disposed of. The silica columns were washed five times with 2 ml isopropanol/hexane (4/96 v/v) and 3 times with 2 ml isopropanol/hexane (6/94 (v/v)). The 1,25-dihydroxy vitamin D was then eluded from the silica columns with two times 2 ml isopropanol/hexane (25/75 v/v) and dried in a nitrogen atmosphere at 37EC or in a vacuum centrifuge. The standard and investigation samples were finally taken up in 20 μl ethanol p.a., in each case with 200 μl mouse-anti-1,25-dihydroxy vitamin D-antibody solution (1:150000 in RRA assay buffer: 50 mM $KH_2PO_4$, 15 mM KCl, 1.25 mM EDTA, 3 mM mercaptoethanol, pH 7.5) and pre-incubated for 1 hour at room temperature—as far as possible at the same time as the application of the 1,25-dihydroxy vitamin D-biotin tracer to the streptavidin treated microtitration plate.

(iii) The wells of the tracer-coated microtitration plate were washed five times in each case with 300 μl Triton™ washing buffer and knocked out onto absorptive paper. Then, 200 μl antibody sample solution from the pre-incubation was transferred into the wells and incubated for 1 hour in the dark and subject to shaking at room temperature. After the removal of the solutions from the wells they were washed five times in each case with 200 μl washing buffer. The quantitative determination was effected analogously to Example 3 by means of 1 hour incubation with 200 μl rabbit-anti-mouse-IgG-peroxidase (1:10000 in washing buffer), at room temperature, five times washing of the wells with 300 μl washing buffer, a colour reaction in the dark with 200 μl TMB substrate solution (ready for use from NOVUM Diagnostika GmbH, Dietzenbach) stopping of the colour reaction after 15 minutes by means of the addition of 50 μl 2 M $H_2SO_4$ and determination of the extinction at 450 nm.

The following table VIII shows the results of the 1,25-dihydroxy vitamin D determination in serum from 11 dialysis patients and six randomly chosen normal persons. For determination of the calibration curve or as standard, there were employed solutions of 1,25-dihydroxy vitamin D in assay buffer with the following concentration: 0, 6.6, 20, 60 and 180 pg/ml (see calibration curve in FIG. 5C).

prepurified on a $SiO_2$ column and purified via HLPC to obtain 1.42 mg (1.6 μmol $C_{58}H_{90}O_6$) dimer, which gives a yield of 12.8% (exact mass 882 D).

HPLC: Krauer Kromasil 100 Sil 7 μm, 250×16 mm, 50 mm Precolumn, t-butanol/$CH_2Cl_2$ (1:1 v/v), 4.5 ml/min. (17 min.)

MS (PI-DICIMS, $NH_3$): 383.3 (M-RCOOH, McLafferty, +H+) 100%, 883.5 ($MH^+$) 20%, 900.5 ($MNH_4^+$, 80%).

TABLE VIII

| Pipetting scheme | Standard 1,25-OH-Vit.D (pg/ml) | Remarks | | OD 450 nm | Douple value | Mean value | Standard deviation |
|---|---|---|---|---|---|---|---|
| 1 | 0 | Calibration curve - | | 0.784 | 0.781 | 0.782 | 0.002 |
| 2 | 6.6 | See FIG. 5c | | 0.732 | 0.741 | 0.737 | 0.006 |
| 3 | 20 | | | 0.682 | | 0.628 | |
| 4 | 60 | | | 0.484 | | 0.484 | |
| 5 | 180 | | | 0.233 | | 0.233 | |
| Control Serum 98-08-295 | 50.1 | Desired range: Mean: S.D.: | 23-63 pg/ml 43.21 pg/ml 6.62 pg/ml | 0.493 | | | |
| Sample Number | Measured value (pg/ml) | | | | | | |
| 1 | 6.5 | Serum samples from | | 0.705 | 0.733 | 0.719 | 0.020 |
| 2 | 39.1 | dialysis patients | | 0.564 | 0.508 | 0.536 | 0.040 |
| 3 | 57.8 | Mean value: | 20.5 | 0.475 | 0.458 | 0.466 | 0.012 |
| 4 | 12.2 | S.D. | 17.2 | 0.672 | 0.687 | 0.679 | 0.010 |
| 5 | 0.3 | Median | 13.4 | 0.776 | 0.774 | 0.775 | 0.002 |
| 6 | 4.0 | | | 0.667 | 0.816 | 0.741 | 0.105 |
| 7 | 13.4 | | | 0.642 | 0.700 | 0.671 | 0.041 |
| 8 | 39.4 | | | 0.565 | 0.504 | 0.535 | 0.043 |
| 9 | 22.1 | | | 0.619 | 0.618 | 0.000 | |
| 10 | 22.6 | | | 0.531 | 0.700 | 0.616 | 0.119 |
| 11 | 8.6 | | | 0.705 | | 0.705 | |
| Comp. samples | | | | | | | |
| 1 | 52.9 | Serum sample from | | 0.502 | 0.464 | 0.483 | 0.027 |
| 2 | 42.6 | normal persons | | 0.518 | 0.525 | 0.522 | 0.005 |
| 3 | 35.3 | Mean value | 46.0 | 0.522 | 0.583 | 0.553 | 0.043 |
| 4 | 32.9 | S.D | 9.7 | 0.571 | 0.556 | 0.563 | 0.010 |
| 5 | 59.2 | Median | 47.8 | 0.410 | 0.514 | 0.462 | 0.073 |
| 6 | 53.1 | | | 0.485 | 0.480 | 0.482 | 0.003 |

FIG. 14 illustrates in a bar chart once again the values found for dialysis and normal patients, in accordance with which values the serum of dialysis patients on average contains significantly less active 1,25-dihydroxy vitamin D. The great variance of the values for the dialysis patients shows also the need to more closely monitor the content of active 1,25-dihydroxy vitamin D in the serum of dialysis patients, in order better to counter the typical consequences of a vitamin D deficiency.

Example 10

Preparation of 25-OH vitamin $D_3$ Dimer Bridged by a Short Hydrocarbon Spacer Group 5 mg 25-OH-vitamin $D_3$-3β-3'amino propylether (12.5 μmol $C_{27}H_{44}O_2$, 400) was reacted with succinic anhydride ($C_4H_4O_3$) in DCC, DMAP, $CH_2Cl_2$. The reaction product was

| 1H-NMR (400 MHz, $CDCl_3$, TMS) | | | |
|---|---|---|---|
| δ | H | Mult | |
| 0.5 | 6 | s | 2 × C18-$CH_3$ |
| 0.9 | 6 | d | 2 × 21-$CH_3$ |
| 1.2 | 12 | s | 2 × $C_{27/28}$ $CH_3$ |
| 2.6 | 4 | s | Succinimid $CH_2$ |
| 4.8 | 2 | d | 2 × C19-H (β) |
| 5.0 | 2 | m | 2 × C3-H |
| 5.1 | 2 | m | 2 × C19-H(α) |
| 6.0 | 2 | d | 2 × C7-H |
| 6.2 | 2 | D | 2 × C6-H |

Example 11

RIA for Determining Competition and Displacement Efficiency

Displacement efficiencies on vitamin D binding protein from goat serum and competition with $^3H$-25OH-vitamin $D_3$ were measured for three vitamin D derivates using a RIA. The tested derivatives were 25-OH-vitamin D, biotinylated 25-OH-vitamin $D_3$ of example 1 and 25-OH-$D_3$ dimer of example 10.

| Conc. [ng/ml] | B/Bo 25-OH-$D_3$ | B/Bo Biotin-25OH-$D_3$ | B/Bo 25-OH-$D_3$ dimer |
|---|---|---|---|
| 0.1 | 100 | 100 | 100 |
| 1 | 92 | 99 | 100 |
| 10 | 33 | 63 | 97 |
| 100 | 10 | 15 | 95 |
| 1000 | 7 | 8 | 83 |

The data show that 25-OH-vitamin D, biotinylated 25-OH-vitamin $D_3$ of example 1 and 25-OH-$D_3$ dimer displacement the tritiated compound from the vitamin D binding protein. The dimer having a short spacer has a lower displacement efficiecy than the corresponding biotinylated compound with the longer spacer group. The corresponding Scatchard plots are shown in FIG. 15. As can be seen from the Scatchard plots, the displacement efficiencies of the compounds of the present invention were all close to 1, which means that each molecule of vitamin D derivate could displace one molecule of the tritiated compound from the vitamin D binding protein. For comparision, compound C in WO 97/24127 (Holick et al.) could only displace the tritiated compound from human vitamin D binding protein when it was present in eleven-fold excess. Moreover, the Scatchard plots show that the displacement efficiencies are linear and parallel over the relevant concentration ranges. The displacement efficiency of the dimer is lower than of the biotinylated 25-OH vitamin D compound, which shows that a hydrocarbon spacer of 0.8 to 4.2 nm length is essential for high affinity and displacement efficiency. A longer spacer group in the vitamin D dimer leads to a higher affinity to DBP. An eleven fold lower affinity on the other hand is typical for vitamin D derivatives lacking the 25 hydroxy group which is essential for high affinity to vitamin D binding protein DBP.

The invention claimed is:

1. A method of measuring the amount of 1α,25-dihydroxy vitamin D in human serum using a competitive protein binding assay, comprising:

i) separating 25-hydroxy vitamin D from 1α,25-dihydroxy vitamin D by binding 1α,25-dihydroxy vitamin D in a sample of the human serum to a material that binds 1α,25-dihydroxy vitamin D and eluting 1α,25-dihydroxy vitamin D from said material to provide a measurement sample, ii) measuring the displacement of a vitamin D derivative of formula (I) from an antibody that specifically binds 1α,25-dihydroxy vitamin D by adding an amount of the measurement sample to an amount of the antibody having the vitamin D derivative of formula (I) bound thereto,

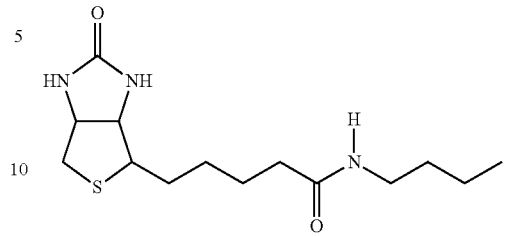

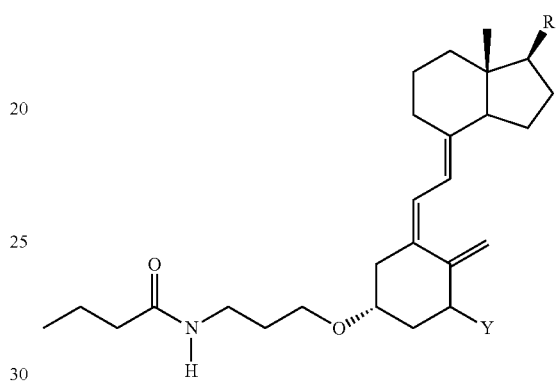

(I)

wherein:

R represents a 25-hydroxylated side-group of vitamin $D_2$ or of vitamin $D_3$, and Y represents hydroxy; and iii) correlating the measurement of displacement of the vitamin D derivative of formula (I) from said antibody by 1α,25 dihydroxy-vitamin D present in the measurement sample to a measurement of displacement of the vitamin D derivative of formula (I) from the antibody by a known quantity of the 1α,25-dihydroxy vitamin D to determine the amount of 1α,25-dihydroxy vitamin D in the sample.

2. The method of claim 1, wherein said competitive protein binding assay is selected from the group consisting of an enzyme immunoassay, an enzyme-linked immunosorbent assay, a radioimmunoassay, an immunoradiometric assay, a luminescence assay, a fluorescence immunoassay and an immunofluorometric assay.

3. The method of claim 1, wherein the method is a sandwich immunoassay, selected from the group consisting of immunoradiometric assay, IEMA/EIA, immunoluminometric assay and immunofluorometric assay.

4. A kit for determining the concentration of 1α,25-dihydroxy vitamin D in a sample of human serum by an immune-based competitive protein binding assay, comprising a standardized quantity of a solid vitamin D derivative of formula (I) or a standardized solution of a vitamin D derivative of formula (I),

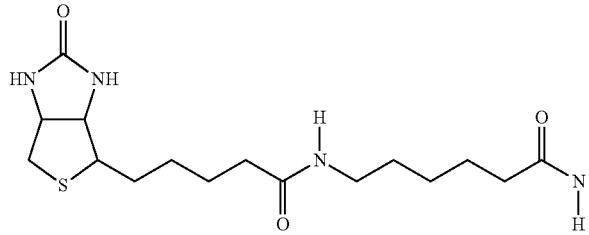
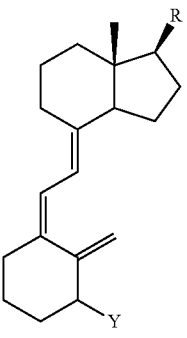

wherein R represents a 25-hydroxylated side-group of vitamin $D_2$ or of vitamin $D_3$, and Y represents hydroxy;

a standardized quantity of an antibody that specifically binds 1α,25-dihydroxy vitamin D;

and a known quantity of 1α,25-dihydroxy vitamin D, so that the displacement of the vitamin D derivative of formula (I) from said antibody as effected by the 1α,25-dihydroxy vitamin D present in the measurement sample can be correlated to the displacement of the vitamin D derivative of formula (I) from said antibody as effected by the addition of a known quantity of the 1α,25-dihydroxy vitamin D to determine the amount of 1α,25-dihydroxy vitamin D present in human serum.

5. The kit of claim 4, further comprising a material that can bind 1α,25-dihydroxy vitamin D for separation of 25-hydroxy vitamin D from 1α,25-dihydroxy vitamin D.

6. The kit of claim 4, wherein said competitive protein binding assay is selected from the group consisting of an enzyme immunoassay, an enzyme-linked immunosorbent assay, a radioimmunoassay, an immunoradiometric assay, a luminescence assay, a fluorescence immunoassay and an immunofluorometric assay.

7. The kit of claim 4, wherein said competitive binding assay is a sandwich immunoassay, selected from the group consisting of immunoradiometric assay, IEMA/EIA, immunoluminometric assay and immunofluorometric assay.

8. The kit of claim 4 comprising a solid phase selected from the group consisting of a microtitration plate, another solid carrier, a microparticle, a polymeric material, and a cellulose.

9. The kit of claim 2, in which the solid phase is a microparticle comprising agarose.

10. The kit of claim 2, in which the solid phase is a magnetic microparticle.

11. The kit of claim 5, in which the material that can bind 1α,25-dihydroxyvitamin D for separation of 25-hydroxy vitamin D from 1α,25-dihydroxy vitamin D is one suitable for packing into a chromatographic column or one that is provided in a chromatographic column.

* * * * *